US008410115B2

(12) United States Patent
Lieberburg

(10) Patent No.: US 8,410,115 B2
(45) Date of Patent: Apr. 2, 2013

(54) METHODS OF TREATING INFLAMMATORY AND AUTOIMMUNE DISEASES WITH ALPHA-4 INHIBITORY COMPOUNDS

(75) Inventor: Ivan Lieberburg, Berkeley, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 168 days.

(21) Appl. No.: 11/711,874

(22) Filed: Feb. 28, 2007

(65) Prior Publication Data

US 2008/0044382 A1    Feb. 21, 2008

Related U.S. Application Data

(60) Provisional application No. 60/777,797, filed on Feb. 28, 2006.

(51) Int. Cl.
*A01N 43/54*    (2006.01)
*C07D 239/42*   (2006.01)
*C07D 401/04*   (2006.01)
*A61K 31/505*   (2006.01)
*A61K 31/44*    (2006.01)
*A01N 43/40*    (2006.01)

(52) U.S. Cl. .................. 514/256; 514/275; 514/351
(58) Field of Classification Search .................. 514/256, 514/275, 351
See application file for complete search history.

(56) References Cited

U.S. PATENT DOCUMENTS

| | | | |
|---|---|---|---|
| 5,840,299 | A | 11/1998 | Bendig et al. |
| 6,033,665 | A | 3/2000 | Yednock |
| 6,229,011 | B1 | 5/2001 | Chen et al. |
| 6,238,859 | B1 | 5/2001 | Lüke et al. |
| 6,388,084 | B1 | 5/2002 | Kaplan et al. |
| 6,551,593 | B1 | 4/2003 | Ringler et al. |
| 6,602,503 | B1 | 8/2003 | Lobb et al. |
| 6,605,602 | B1 | 8/2003 | Vats |
| 7,008,949 | B2 | 3/2006 | Konradi et al. |
| 7,026,328 | B2 | 4/2006 | Konradi et al. |
| 7,026,501 | B2 | 4/2006 | Kawaguchi et al. |
| 7,101,855 | B2 | 9/2006 | Dressen et al. |
| 2002/0197233 | A1 | 12/2002 | Relton et al. |
| 2003/0176498 | A1 | 9/2003 | Kawaguchi et al. |
| 2004/0009169 | A1 | 1/2004 | Taylor et al. |
| 2004/0138243 | A1 | 7/2004 | Konradi et al. |
| 2004/0142954 | A1 | 7/2004 | Konradi et al. |
| 2006/0009385 | A1 | 1/2006 | Hoffman et al. |
| 2006/0013799 | A1 | 1/2006 | Konradi et al. |
| 2007/0142416 | A1 | 6/2007 | Semko et al. |
| 2008/0058357 | A1 | 3/2008 | Smith et al. |
| 2009/0169477 | A1 | 7/2009 | Panzara et al. |
| 2009/0216107 | A1 | 8/2009 | Rubin et al. |

FOREIGN PATENT DOCUMENTS

| | | |
|---|---|---|
| WO | WO 2006/112951 | 10/2006 |
| WO | WO 2007/041270 | 4/2007 |
| WO | WO 2007/100763 A2 | 9/2007 |
| WO | WO 2007/100770 A2 | 9/2007 |
| WO | WO 2007/101165 | 9/2007 |
| WO | WO 2007/103112 A2 | 9/2007 |

OTHER PUBLICATIONS

Van Assche et al. New England Journal of Medicine. Jul. 2005, vol. 353, No. 4, pp. 362-368.*
Pestalozza et al. Multiple Sclerosis. 2005. vol. 11, pp. 390-394.*
Abraham et al., "A Small-Molecule, Tight-binding Inhibitor of the Integrin $\alpha_4\beta_1$ Blocks Antigen-induced Airway Responses and Inflammation in Experimental Asthma in Sheep," *Am. J. Respir. Crit. Care Med.*, 162:603-611 (2000).
Agostini et al., "Genotype Profile of Human Polyomavirus JC Excreted in Urine of Immunocompetent Individuals," *J. Clin. Microbiol.* 34:159-164 (1996).
Albrecht et al., "Highly active antiretroviral therapy significantly improves the prognosis of patients with HIV-associated progressive multifocal leukoencephalopathy," *AIDS*, 12:1149-1154 (1998).
Baron et al., "Surface Expression of $\alpha 4$ Integrin by CD4 T Cells Is Required for Their Entry Into Brain Parenchyma," *J. Exp. Med.* 177:57-68 (1993).
Berger et al., "Predictive Factors for Prolonged Survival in Acquired Immunodeficiency Syndrome-Associated Progressive Multifocal Leukoencephalopathy," *Annals of Neurology*, 44:341-349 (1998).
Brocke et al., "Antibodies to CD44 and Integrin $\alpha 4$, but not L-selection, Prevent Central Nervous System Inflammation and Experimental Encephalomyelitis by Blocking Secondary Leukocyte Recruitment," *Proc. Natl. Acad. Sci.* 96:6896-6901 (1999).
Brück et al., "Inflammatory Central Nervous System Demyelination: Correlation of Magnetic Resonance Imaging Findings with Lesion Pathology,"*Annals of Neurology*, 42:783-793 (1997).
Clifford et al., "HAART Improves Prognosis in HIV-associated Progressive Multifocal Leokoencephalopathy,"*Neurology*52:623-625 (1999).
Collazos, "Opportunistic Infections of the CNS in Patients with AIDS,"*CNS Drugs* 17:869-887 (2003).
Co-Pending U.S. Appl. No. 11/713,000, filed Mar. 2, 2007.
Co-Pending U.S. Appl. No. 11/711,628, filed Feb. 28, 2007.
Crowder et al., "Successful Outcome of Progressive Multifocal Leukoencephalopathy in a Renal Transplant Patient," *American Journal of Transplantation*, 5:1151-1158 (2005).
Demeter, "JC, BK, and Other Polyomaviruses; Progressive Multifocal Leukoencephalopathy," *Mandell, Douglas and Bennett's Principles and Practice of Infectious Diseases*, Mandell et al. Eds., 4th Ed., New York, NY: Churchill Livingstone; 1995:1400-1406.

(Continued)

*Primary Examiner* — Samira Jean-Louis
(74) *Attorney, Agent, or Firm* — Finnegan, Henderson, Farabow, Garrett & Dunner LLP

(57) ABSTRACT

Alpha 4 inhibitors are used in treatment of inflammatory and autoimmune diseases, such as multiple sclerosis, Crohn's Disease, rheumatoid arthritis and asthma. Rare occurrences of progressive multifocal leucoencephalopathy during treatment with an alpha-4 agent suggest the possibility that it may be related to such treatment. Monitoring for the JC virus and educating caregivers and patients about the manifestations of progressive multifocal leucoencephalopathy can improve the safety of alpha 4 inhibitor therapy.

80 Claims, No Drawings

OTHER PUBLICATIONS

Dörries et al., "Association of Human Polyomavirus JC with Peripheral Blood of Immunoimpaired and Healthy Individuals," *Journal of NeuroVirology*, 9(suppl. 1);81-87 (2003).

Dörries et al., "Infection of Human Polyomaviruses JC and BK in Peripheral Blood Leukocytes from Immunocompetent Individuals," *Virology*, 198:59-70 (1994).

Dubois et al., "Detection of JC Virus DNA in the Peripheral Blood Leukocytes of HIV-infected Patients," *AIDS* 10:353-358 (1996).

Dworkin et al., "A Review of Progressive Multifocal Leukoencephalopathy in Persons With and Without AIDS, " *Curr. Clin. Top. Infect. Dis.* 22:181-195 (2002).

Engelhardt, et al. "Therapeutic targeting of α4-integrins in chronic inflammatory diseases: tipping the scales of risk towards benefit?" *Eur. J. Immunol.*, 35:2268-2273 (2005).

Ernst et al., "Progressive Multifocal Leukoencephalopathy and Human Immunodeficiency Virus-associated White Matter Lesions in AIDS: Magnetization Transfer MR Imaging," *Radiology* 210:539-543 (1999).

Ferrante et al., "Detection of JC Virus DNA in Cerebrospinal Fluid from Multiple Sclerosis Patients," *Multiple Sclerosis*, 4:49-54 (1998).

Geschwind et al., "The Relative Contributions of HAART and Alpha-interferon for Therapy of Progressive Multifocal Leukoencephalopathy in AIDS," *J. Neurovirol.* 7:353-357 (2001).

Gibson et al., "Detection of JC Virus DNA in the Cerebrospinal Fluid of Patients With Progressive Multifocal Leukoencephalopathy," *J. Med. Virol.* 39:278-281 (1993).

Henson et al., "Amplification of JC Virus DNA from Brain and Cerebrospinal Fluid of Patients with Progressive Multifocal Leukoencephalopathy," *Neurology* 41:1967-1971 (1991).

Hijazi et al., "Pharmacokinetics, Safety, and Tolerability of R411, a Dual αβ1-α4β7 Integrin Antagonist After Oral Administration at Single and Multiple Once-Daily Ascending Doses in Healthy Volunteers," *J. Clin. Pharmacol.*, 44:1368-1378 (2004).

Hochberg, "A Sharper Bonferroni Procedure for Multiple Tests of Significance," *Biometrika* 75:800-802 (1988).

Hoffmann et al., "Progressive Multifocal Leucoencephalopathy with Unusual Inflammatory Response During Antiretroviral Treatment," *J. Neurol. Neurosurg. Psychiatry* 74:1142-1144 (2003).

Hurley et al., "Identification of HIV-Associated Progressive Multifocal Leukoencephalopathy: Magnetic Resonance Imaging and Spectroscopy," *J. Neuropsychiatry Clin. Neurosci.* 15:1-6 (2003).

IFNB Multiple Sclerosis Study Group, "Interferon Beta-1b is Effective in Relapsing-Remitting Multiple Sclerosis. I. Clinical Results of a Multicenter, Randomized, Double-blind, Placebo-controlled Trial," *Neurology* 43:655-661 (1993).

International Search Report from PCT/US2007/05265, dated Oct. 2, 2007.

International Search Report from PCT/US2007/004923, dated Sep. 22, 2008.

International Search Report from PCT/US2007/004943, dated Oct. 3, 2008.

Isaac et al., "Multiple Sclerosis: A Serial Study Using MRI in Relapsing Patients," *Neurology* 38:1511-1515 (1988).

Jacobs et al., "Intramuscular Interferon Beta-1a for Disease Progression in Relapsing Multiple Sclerosis," *Annals of Neurology*, 39:285-294 (1996).

Johnson et al., "Copolymer 1 Reduces Relapse Rate and Improves Disability in Relapsimg-Remitting Multiple Sclerosis: Results of a Phase III Multicenter, Double-blind, Placebo-controlled Trial," *Neurology* 45:1268-1276 (1995).

Kappos et al., "Predictive Value of Gadolinium-enhanced Magentic Resonance Imaging for Relapse Rate and Changes in Disability or Impairment in Multiple Sclerosis: A Meta-analaysis," *The Lancet*, 353:964-969 (1999).

Kent et al., "A Monoclonal Antibody to α4 Integrin Suppresses and Reverses Active Experimental Allergic Encephalomyelitis," *J. Neuroimmunol.* 58:1-10 (1995).

Khoury et al., "Longitudinal MRI in Multiple Sclerosis: Correlation Between Disability and Lesion Burden," *Neurology* 44:2120-2124 (1994).

Kitamura et al., "High Incidence of Urinary JC Virus Excretion in Nonimmunosuppressed Older Patients," *J. Infect. Dis.* 161:1128-1133 (1990).

Kleinschmidt-DeMasters et al., "Progressive Multifocal Leukoencephalopathy Complicationg Treatment with Natalizumab and Interferon Beta-1a for Multiple Sclerosis," *N. Engl. J. Med.* 353:369-374 (2005).

Knowles et al., "Prevalence of Long-Term BK and JC Excretion in HIV-Infected Adults and Lack of Correlation With Serological Markers," *J. Med. Virol.* 59:474-479 (1999).

Knowles et al., "The JC Virus Antibody Response in Serum and Cerebrospinal Fluid in Progressive Multifocal Leucoencephalophy," *Clinical and Diagnostic Virology*, 4:183-194 (1995).

Koralnik, "New Insights Into Progressive Multifocal Leukoencephalopathy," *Current Opinion in Neurology*, 17:365-370 (2004).

Kozovska et al., "Interferon Beta Induces T-helper 2 Immune Deviation in MS," *Neurology* 53:1692-1697 (1999).

Langer-Gould et al., "Progressive Multifocal ALeukoencephalopathy in a Patient Treated with Natalizumab," *N. Eng. J. Med.* 353:375-381 (2005).

Mamidi et al., "Central Nervous System Infections in Individuals with HIV-1 Infection," *J. Neurovirol.* 8:158-167 (2002).

McDonald et al., "Recommended Diagnostic Criteria for Multiple Sclerosis: Guidelines from the International Panel on the Diagnosis of Multiple Sclerosis," *Annals of Neurology*, 50:121-127 (2001).

McFarland et al., "The Role of MRI as a Surrogate Outcome Measure in Multiple Sclerosis," *Multiple Sclerosis* 8:40-51 (2002).

Miller et al., "A Controlled Trial of Natalizumab for Relapsing Multiple Sclerosis," *N. Engl. J. Med.* 348:15-23 (2003).

Molyneux et al., "Correlations between Monthly Enhanced MRI Lesion Rate and Changes in T2 Lesion Volume in Multiple Sclerosis," *Annals of Neurology*, 43:332-339 (1998).

Olsen et al., "White Matter Disease in AIDS: Findings at MR Imaging," *Radiology* 169:445-448 (1988).

Padgett et al., "Virologic and Serologic Studies of Progressive Multifocal Leukoencephalopathy," *Prog. Clin. Biol. Res.* 105:107-117 (1983).

Polman et al., "A Randomized, Placebo-Controlled Trail of Natalizumab for Relapsing Multiple Sclerosis," *N. Engl. J. Med.*, 354(9):899-910 (2006).

Post et al., "Progressive Multifocal Leukoencephalopathy in AIDS: Are There Any MR Findings Useful to Patient Management and Predictive of Patient Survival?," *Am. J. Neuroradiol.* 20:1896-1906 (1999).

PRISMS Study Group, "Randomised Double-blind Placebo-controlled Study of Interferon β-1a in Relapsing/Remitting Multiple Sclerosis," *The Lancet* 352:1498-1504 (1998).

Przepiorka et al., "Successful Treatment of Progressive Multifocal Leukoencephalopathy with Low-Dose Interleukin-2," *Bone Marrow Transplant*, 20:983-987 (1997).

Redington et al., "Viral Infections of the Nervous System, 2002," *Arch. Neurol*: 59:712-718 (2002).

Rep et al., "Recombinant Interferon-β Blocks Proliferation but Enhances Interleukin-10 Secretion by Activated Human T-Cells," *J. Neuroimmunol.* 67:111-118 (1996).

Rudick et al., "Incidence and Significance of Neutralizing Antibodies to Interferon Beta-1a in Multiple Sclerosis," *Neurology* 50:1266-1272 (1998).

Rudick et al., "Natalizumab plus Interferon Beta-1a for Relapsing Multiple Sclerosis," *N. Engl. J. Med.*, 354(9):911-923 (2006).

Salmaggi et al., "Reversal of CSF Positivity for JC Virus Genome by Cidofovir in a Patient with Systemic Lupus Erthematosus and Progressive Multifocal Leukoencephalopathy," *Neurol. Sci.* 22:17-20 (2001).

Schuurman et al., "Normal human immunoglobulin G4 is bispecific: it has two different antigen-combining sites," *Immunology*, 97:693-698 (1999).

Seth et al., "Advances in the Biology of JC Virus and Induction of Progressive Multifocal Leukoencephalopathy," *J. Neurovirol.* 9:236-246 (2003).

Shitrit et al.,"Progressive Multifocal Leukoencephalopathy in Transplant Recipients," *Transpl. Int.* 17:658-665 (2005).

Simon et al., "A Longitudinal Study of T1 Hypointense Lesions in Relapsing MS," *Neurology* 55:185-192 (2000).

Sundsfjord et al., "BK and JC Viruses in Human Immunodeficiency Virus Type 1-Infected Persons: Prevalence, Excretion, Viremia, and Viral Regulatory Regions," *J. Infect. Dis.* 169:485-490 (1994).

Tantisiriwat et al., "Progressive Multifocal Leukoencephalopathy in Patients with AIDS Receiving Highly Active Antiretroviral Therapy," *Clin. Infect. Dis.* 28:1152-1154 (1999).

Tenser, R.B. et al., "Natalizumab for Relapsing Multiple Sclerosis," *N. Engl. J. Med.*, 354(22): 2387-2389 (2006).

Thompson et al., " Major Differences in the Dynamics of Primary and Secondary Progressive Multiple Sclerosis," *Ann. Neurol.* 29:53-62 (1991).

Thompson et al., "Serial Gadolinium-Enhanced MRI in Relapsing/Remitting Multiple Sclerosis of Varying Disease Duration," *Neurology* 42:60-63 (1992).

Tornatore et al., "Detection of JC Virus DNA in Peripheral Lymphocytes from Patients with and without Progressive Multifocal Leukoencephalopathy," *Annals of Neorology*, 31:454-462 (1992).

Vago et al., "JCV-DNA and BKV-DNA in the CNS Tissue and CSF of AIDS Patients and Normal Subjects. Study of 41 Cases and Review of the Literature," *J. Acquir. Imm. Defic. Syndr. Hum. Retrovirol.* 12:139-146 (1996).

Van Assche et al., "Progressive Multifocal Leukoencephalophy after Natalizumab Therapy for Crohn's Disease," *N. Eng. J. Med.*, 353:362-368 (2005).

Van Assche et al., "Physiological Basis for Novel Drug Therapies Used to Treat the Inflammatory Bowel Diseases: 1. Immunology and therapeutic potential of antiadhesion molecule therapy in inflammatory bowel disease," *Am. J. Physiol. Gastrointest. Liver Physiol.*, 288:G169-G174 (2005).

von Andrian et al., "$\alpha_4$ Integrins as Therapeutic Targets in Autoimmune Disease" *N. Engl. J. Med.*, 348(1):68-72.

Weber et al., "Progressive Multifocal Leukoencephalopathy Disgnosed by Amplification of JC Virus-specific DNA from Cerebrospinal Fluid," *AIDS* 8:49-57 (1994).

Weber et al., "Specific Diagnosis of Progressive Multifocal Leukoencephalopathy by Polymerase Chain Reaction," *J. Infect. Dis.* 169:1138-1141 (1994).

Whitaker et al., "Outcomes Assessment in Multiple Sclerosis Clinical Trials: a Critical Analysis," *Multiple Sclerosis*, 1:37-47 (1995).

Willoughby et al., "Serial Magnetic Resonance Scanning in Multiple Sclerosis: A Second Prospective Study in Relapsing Patients," *Annals of Neurology*, 25:43-49 (1989).

Yednock et al., "Prevention of Experimental Autoimmune Encephalomyelitis by Antibodies Against $\alpha 4\beta 1$ Integrin," *Nature* 356:63-66 (1992).

Yousry et al. "Evaluation of Patients Treated with Natalizumab for Progressive Multifocal Leukoencephalopathy," *N. Engl. J. Med.*, 354:924-33 (2006).

Zang et al., "Regulation of Chemokine Receptor CCR5 and Production of RANTES and MIP-1$\alpha$ by Interferon-$\beta$," *J. Neuroimmunol.* 112:174-180 (2001).

Office Action dated Dec. 24, 2009, for U.S. Appl. No. 11/713,000.

Berger, Jr. et al., "Progressive multifocal leukoencephalopathy and natalizumab—Unforseen consequences"; New England Journal of Medicine Jul. 28, 2005; 353(4): pp. 414-416, 2005.

Brennan, D.C., et al., "Incidence of BK with tracrolimus versus cyclosporine and impact of preemptive immunosuppression reduction," American Journal of Transplantation; 5(3): pp. 582-594, 2005.

Enns et al., "Safety, Tolerability and Immunogenicity of Natalizumab ina Phase III Study of Active Crohn's Disease Therapy," Gastroenterology 126 (4, Suppl. 2): pA462 2004.

Hohlfeld et al., "Basic Principles of Immunotherapy for Neurologic Diseases," Seminars in Neurology 23(2):121-131, 2003.

International Search Report for PCT/US06/06723 (WO 2006/112951) dated Sep. 18, 2006.

Kieseier et al.,"Current Disease-Modifying Therapies in Multiple Sclerosis," Seminars in Neurology 23(2): 133-146, 2003.

Langer-Gould, A. et al. "Progressive Multifocal Leukoencephalopathy in a Patient Treated with Natalizumab."; The New England Journal of Medicine, 353(4): pp. 375-381,2005.

Office Action dated Jul. 21, 2010, in co-pending U.S. Appl. No. 11/711,628.

Office Action dated Jul. 20, 2010, in U.S. Appl. No. 11/713,000.

Office Action dated Sep. 12, 2008, in U.S. Appl. No. 11/713,000.

Public Health Advisory—Suspended Marketing of Tysabri (Natalizumab), Feb. 28, 2005.

Office Action dated Aug. 4, 2011, for U.S. Appl. No. 12/757,305.

Office Action dated Feb. 15, 2012, for U.S. Appl. No. 12/757,305.

Office Action dated Mar. 30, 2011, for U.S. Appl. No. 11/711,628.

Office Action mailed Dec. 22, 2011, for U.S. Appl. No. 11/713,000.

* cited by examiner

METHODS OF TREATING INFLAMMATORY AND AUTOIMMUNE DISEASES WITH ALPHA-4 INHIBITORY COMPOUNDS

This application claims the benefit of U.S. Provisional Application No. 60/777,797 filed Feb. 28, 2006, which is hereby incorporated by reference herein in its entirety for any purpose.

TECHNICAL FIELD

The invention relates to methods of treating inflammatory and autoimmune diseases with alpha-4 inhibitory compounds. These methods improve the safety of treatment by informing and monitoring patients undergoing treatment with such therapeutics.

BACKGROUND ART

The migration of lymphocytes from the peripheral blood across the blood brain barrier has been reported to initiate the development of several central nervous system (CNS) inflammatory diseases. Lymphocyte entry into the CNS is mediated by cellular adhesion molecules (O'Neill et al., *Immunology* 72:520-525 (1991); Raine et al., *Lab. Invest.* 63:476-489 (1990); Yednock et al., *Nature* 356:63-66 (1992); Baron et al., *J. Exp. Med.* 177:57-68 (1993); Steffen et al., *Am. J. Path.* 145:189-201 (1994); Christensen et al., *J. Immunol.* 154:5293-5301 (1995)).

Cellular adhesion molecules present on the cell surface mediate the direct binding of one cell to another (Long et al., *Exp. Hematol.* 20:288-301 (1992)). The integrin and immunoglobulin supergene families of adhesion molecules regulate lymphocyte traffic into the CNS (Hemler et al., *Annu. Rev. Immunol.* 8:365-400 (1990); Springer et al., *Cell* 76:301-314 (1994); Issekutz et al., *Curr. Opin. Immunol.* 4:287-293 (1992)). Adhesion molecules have been widely reported to mediate inflammatory and autoimmune diseases, for example, asthma, Alzheimer's disease, atherosclerosis, AIDS dementia, diabetes, inflammatory bowel disease, multiple sclerosis, rheumatoid arthritis, tissue transplantation rejection, and tumor metastasis.

Integrins are heterodimers of non-covalently linked $\alpha$ and $\beta$ chains (Hemler et al., *Annu. Rev. Immunol.* 8:365-400 (1990)). The $\alpha 4\beta 1$ (also called very late activation antigen-4 VLA-4) and $\alpha 4\beta 7$ integrins are present on the surface of most types of white blood cells, where they mediate white cell binding to endothelial cells by interacting with their cognate receptors, vascular cell adhesion molecule-1 (VCAM-1) and mucosal addressing cellular adhesion molecule-1 (MAd-CAM-1), on the endothelial cell surface. Integrins are believed to play an important role in immune cell adhesion to the endothelial cell layer on blood vessels, facilitating their subsequent migration into inflamed tissues. Several studies implicate VLA-4 and, in particular the $\alpha 4$ integrin subunit, in CNS inflammation (Yednock et al., *Nature* 356:63-66 (1992); Baron et al., *J. Exp. Med.* 177:57-68 (1993); Steffen et al., *Am. J. Path.* 145:189-201 (1994); Christensen et al., *J. Immunol.* 154:5293-5301 (1995). It has also been reported that VCAM-1 expression is elevated in inflamed brain tissue relative to normal brain tissue (Cannella and Raine, *Ann. Neurol.* 37:424-435 (1995); Washington et al., *Ann. Neurol.* 35:89-97 (1994); Dore-Duffy et al., *Frontiers in Cerebral Vascular Biology: Transport and Its Regulation*, 243-248 (Eds. Drewes & Betz, Plenum, N.Y. 1993)).

The interaction between $\alpha 4\beta 1$ and its targets is a component of the inflammation that takes place in the CNS of patients with multiple sclerosis (MS). Under normal conditions, VCAM-1 is not expressed in the brain parenchyma. However, in the presence of pro-inflammatory cytokines, VCAM-1 is upregulated on endothelial cells and on microglial cells near the sites of inflammation (Elices et al., *Cell* 60:577-584 (1990); Lobb and Hemler, *J. Clin. Invest.* 94:1722-1728 (1994); Peterson et al., *J. Neuropathy Exp. Neurol.* 61:539-546 (2002)). Further, osteopontin, which exhibits many properties of a proinflammatory cytokine, is also upregulated in MS lesions (Chabas et al., *Science* 294:1731-1735 (2001)).

MS is a serious and disabling inflammatory and autoimmune disease of young adults, with a peak age of onset in the third decade of life. Most individuals present with the relapsing-remitting form of the disease and experience recurrent attacks, which, over time, result in accumulating permanent physical disability and cognitive decline. About 70% of these individuals will eventually enter a phase of progressive neurological decline (secondary progressive MS), with or without superimposed relapses. Current treatments are minimally effective for secondary progressive MS. The majority of patients suffer permanent neurological dysfunction and, on average, have a life expectancy of six to seven years after the onset of disease.

Currently, four therapies are approved in the United States for the treatment of relapsing forms of MS. The interferons, Betaseron® (interferon $\beta$-1b SC (subcutaneous)), AVONEX® (interferon $\beta$-1a IM (intramuscular)), and Rebif® (interferon $\beta$-1a SC), are cytokines with antiviral, antiproliferative, and immunomodulatory activities. Copaxone® (glatiramer acetate) is a mixture of synthetic polypeptides with a poorly understood mechanism of action. The $\beta$-interferons can produce serious adverse events and some evidence suggests that copaxone is ineffective (Munari, et al., *The Cochrane Library*, Issue 1, Chichester, UK: John Wiley & Sons, Ltd. (2004)).

Serious adverse events of $\beta$-interferons include rare reports of hypersensitivity reactions, depression and suicide, decreased peripheral blood counts, hepatic injury, cardiomyopathy, and various autoimmune disorders (Betaseron Package Insert, 2003; Rebif Package Insert, 2004; AVONEX® Package Insert, 2005). The development of neutralizing antibodies to interferons is associated with a loss of efficacy. Antibodies that develop to a $\beta$-interferon cross-react with other interferons leading to loss of efficacy for the entire class in such patients (IFNB MS Study Group, *Neurology* 47:889-894 (1996); PRISMS Study Group, *Neurology* 56:1628-1636 (2001); Kappos et al., *Neurology* 65:40-47 (2005)). As a result, in the United States alone, over 50,000 patients who were previously treated no longer receive therapy. Thus, there is a large group of patients with active MS who are currently not receiving any approved therapy.

Among those patients who do receive treatment, a significant number continue to experience disease activity, as observed clinically and by magnetic resonance imaging (MRI). Although a variety of therapeutic strategies are currently used in clinical practice to manage breakthrough disease while on treatment (e.g., switching therapy, changing dose and frequency of interferon, combination therapy), the similar efficacy between available medications and lack of clinical data demonstrating the effectiveness of any of these strategies in breakthrough patients makes the decision of what to do for these patients largely empirical. Each of the partially effective approved medications leads to an approximately 30% reduction in relapse rate and limited impact on disability progression (IFNB MS Study Group, *Neurology* 43:655-661 (1993); Jacobs et al., *Ann. Neurol.* 39:285-289

(1996); PRISMS Study Group, *Lancet* 352:1498-1504 (1998)); Johnson et al., *Neurology* 45:1268-1276 (1995)). Data from the Phase 3 trials of β-interferon in MS show that 62% to 75% of subjects experienced at least one relapse during these 2-year trials despite interferon treatment (IFNB MS Study Group, *Neurology* 43:655-661 (1993); Jacobs et al., *Ann. Neurol.* 39:285-289 (1996); PRISMS Study Group, *Lancet* 352:1498-1504 (1998)). Similarly, 66% of subjects in the Phase 3 MS trial of glatiramer acetate experienced at least one relapse during the 2-year period, a proportion that was not significantly different from placebo (Johnson et al., *Neurology* 45:1268-1276 (1995)).

Progressive Multifocal Leukoencephalopathy (PML) is a severe, rapidly progressive disease that destroys the myelin coating which protects nerve cells. PML occurs almost exclusively in severely immunosuppressed patients and is frequently associated with lymphoproliferative and other chronic diseases, such as AIDS, Hodgkin's disease, chronic lymphocytic leukemia, sarcoidosis, tuberculosis, systemic lupus erythematosis, and organ transplantation. JC virus (JCV) is the etiological agent of PML and may result from a primary infection or follow reactivation of latent virus.

Natalizumab, an α4-integrin antagonist, has been used successfully to treat diseases with inflammatory and/or autoimmune components, for example, MS, Crohn's Disease, and rheumatoid arthritis. There are three known cases of PML occurring during or after administration of natalizumab, two proved fatal and one patient recovered. All three cases occurred in patients on concomitant medications which may have contributed to immunosuppression.

Thus, there is a need in the art for determining the relationship between alpha-4 inhibitor therapy and the occurrence of PML and for safer methods of treating patients with alpha-4 inhibitor compounds that take into account the possibility of contracting PML.

SUMMARY

The invention provides safer methods of using an alpha-4 inhibitory compound to treat patients with inflammatory and autoimmune diseases. Specifically, the invention provides a method of using an alpha-4 inhibitory compound to treat a patient with an inflammatory or autoimmune disease by administering a pharmaceutically effective amount of an alpha-4 inhibitory compound, monitoring the patient for at least one indicator of progressive multifocal leukoencephalopathy, and discontinuing the administration of the alpha-4 inhibitory compound in the presence of the at least one indicator of progressive multifocal leukoencephalopathy, wherein the monitoring improves the safety of the treatment.

The invention also provides a method of using an alpha-4 inhibitory compound to treat a patient with an inflammatory or autoimmune disease by removing a sample of blood from the patient, testing the plasma or serum in the sample for the presence of IgG antibodies to JCV, initiating treatment of the patient with an alpha-4 inhibitory compound, monitoring the patient for symptoms of JCV, and discontinuing the administration of the alpha-4 inhibitory compound in the presence of at least one indicator of progressive multifocal leukoencephalopathy, wherein the testing and monitoring improves the safety of the treatment. If the sample is negative for JCV, the monitoring may further comprise measuring the amount of IgM and IgG antibodies in the plasma or serum to detect seroconversion. If the sample is positive for JCV, the monitoring may further comprise measuring the amount of IgG in the plasma or serum to detect an increase in titer. In either case, the monitoring may further comprise monitoring plasma, serum, urine, and/or CSF for JCV. In either case, the monitoring may also comprise testing for at least one symptom chosen from clinical and radiologic symptoms.

The invention further provides informing the prescribing physician about the mental and physical symptoms of progressive multifocal leukoencephalopathy, informing the patient about the mental and physical symptoms of progressive multifocal leukoencephalopathy, and instructing the patient to report to the physician in the presence of at least one symptom.

In an embodiment, the patient is monitored to detect an increasing JCV titer. The monitoring process may comprise serially removing samples of the patient's blood, measuring the amount of IgG antibodies to JCV in the samples, and comparing the amounts of antibody in the samples to those of the series. When the comparison detects an increasing titer of JCV, a sample of the patient's cerebrospinal fluid can be removed and tested for the presence of IgG antibodies to JCV. This method can also be practiced by monitoring the patient by testing for clinical symptoms of progressive multifocal leukoencephalopathy, for example, new or worsening, i.e., progressing, neurological symptoms, or by testing for radiologic symptoms using, e.g., nuclear magnetic resonance. When progressive multifocal leukoencephalopathy is detected, the patient can be treated by antiviral therapy, for example, by administering therapeutically effective doses of cytosine arabinoside and/or cidofovir.

The methods of the invention are suitable for treating inflammatory and autoimmune diseases, including both the relapsing remitting and the chronic progressive forms of multiple sclerosis; inflammatory bowel disease; and rheumatoid arthritis. In an embodiment, the patient is treated with an alpha-4 inhibitory compound as a monotherapy without an immunosuppressive or antineoplastic agent.

DETAILED DESCRIPTION OF THE INVENTION

Brief Description of the Embodiments

Definitions

The terms used herein have their ordinary meanings, as set forth below, and can be further understood in the context of the specification.

The term "alpha 4 inhibitory compound" as used herein denotes a non-antibody compound that may bind either or both α4β1 (also called very late activation antigen-4, VLA-4) and α4β7 integrins and block their interactions with their cognate receptors in body tissues, the interaction of the two mediating certain aspects of various inflammatory and autoimmune diseases.

A "patient" or "subject," used interchangeably herein, refers to a human unless otherwise indicated.

"Treatment" means any administration or application of remedies for disease and includes inhibiting the disease, arresting its development, managing its development and relieving the disease, for example, by causing regression, or restoring or repairing a lost, missing, or defective function or by stimulating an inefficient process.

"Natalizumab" or "Tysabri®" is a humanized antibody against VLA-4 as described in U.S. Pat. Nos. 5,840,299 and 6,033,665, which are herein incorporated by reference in their entireties. Also contemplated herein are other antibodies specific for VLA-4, including, but not limited to, immunoglobulins described in U.S. Pat. Nos. 6,602,503 and 6,551,593, and published U.S. Application No. 20020197233 by Relton et al. These antibody can be prepared by the methods disclosed in these documents, by mammalian cell expression systems, and by transgenic animal expression systems, for example, transgenic goats.

A "pharmaceutically effective amount" or "therapeutically effective amount," used interchangeably, is an amount sufficient to cure or at least partially arrest the symptoms of a disease and/or the complications of a disease.

A "serotonin antagonist" refers to any substance that decreases one or more effects of serotonin binding to its receptor.

"Seroconversion" refers to the change of a serologic test from negative to positive, indicating the development of antibodies.

"Titer" is the concentration of an antibody in solution.

Alpha-4 Inhibitory Compounds

Compounds of the present invention are those non-antibody oligopeptidic or non-peptidic synthetic molecules that bind alpha-4 integrins, either alpha4 beta1 or alpha4 beta7 or both (i.e. dual inhibitors), and block their interactions with VCAM-1, MadCAM-1 and/or fibronectin, thus providing alpha-4 inhibitory activity.

Generally, these alpha-4 inhibitors are small molecule alpha-4 integrin inhibitors, many of which are phenylalanine derivatives having an N-terminal capping group and a free-carboxy C-terminus, although esters and salts thereof are known and may be desirable as pro-drugs or to enhance solubility and are within the scope of the present invention. In other embodiments these small molecule inhibitors may be conjugated to polyethylene glycol (PEG) or other biocompatible polymers to provide alpha-4 integrin binding inhibitors that have longer half-lives in the blood stream and that possess other valuable pharmacokinetic properties.

By small molecules it is meant synthetic compounds having molecular weights ranging from about 200 to about 1000, such as from about 300 to about 700. In the case of PEG polymer conjugates of the small molecule alpha-4 inhibitors, this molecular weight refers only to the weight of one "A" group as defined in Group VII herein and does not include the contribution of the PEG polymer. The total weight of the conjugates of Group VII range from about 20 kDA to 70 kDa, such as in the range of 30 kDa to 60 kDa.

Some non-limiting examples of small molecule alpha-4 adhesion inhibitors are described below.

Group I

In one embodiment of the present invention, compounds having alpha-4 integrin inhibitory activity are described and characterized in U.S. Provisional Patent application 60/722,358, filed on Sep. 29, 2005, which is hereby incorporated by reference in its entirety for all purposes, and are compounds of Formula I, a pharmaceutically acceptable salt or ester of any of the foregoing:

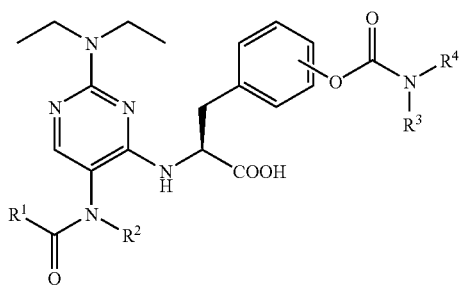

I wherein:

$R_1$ is selected from the group consisting of $C_1$ to $C_4$ alkyl, $C_1$ to $C_4$ haloalkyl, heteroaryl and $-N(R_5)(R_6)$, where $R_5$ and $R_6$ are independently selected from the group consisting of hydrogen, $C_1$ to $C_4$ alkyl or $R_5$ and $R_6$ together with the nitrogen pendent thereto join to form a heterocyclic ring;

$R_2$ is selected from the group consisting of $C_1$ to $C_4$ alkyl, $C_2$ to $C_4$ alkenyl, and $C_2$ to $C_4$ alkynyl; and $R_3$ and $R_4$ are independently $C_1$ to $C_3$ alkyl or $R_3$, $R_4$ together with the nitrogen atom pendent thereto join to form a heterocyclic ring.

The terms used in the Group I compounds are those described in U.S. Provisional Application No. 60/722,358 that include:

"Halo" or "halogen" refers to fluoro, chloro, bromo and iodo and preferably is either fluoro or chloro.

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings wherein the condensed ring may be aryl or heteroaryl. Examples of such heteroaryls include, for instance, furan-2-yl, furan-3-yl, thien-2-yl, thien-3-yl, pyrrol-2-yl, pyrrol-3-yl, pyridyl (2-, 3-, and 4-pyridyls) and the like. In one embodiment, the sulfur and/or nitrogen atoms of the heteroaryl are optionally oxidized (i.e., $-S(O)-$ or $-S(O)_2-$, and/or N-oxides).

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more the rings can be aryl or heteroaryl.

"Alkyl" refers to straight, branched and cyclic alkyl groups preferably having from 1 to 4 carbon atoms and more preferably 1 to 3 carbon atoms. This term is exemplified by groups such as methyl, ethyl, n-propyl, iso-propyl, n-butyl, iso-butyl, sec-butyl, t-butyl, cyclopropyl, cyclobutyl, and methylenecyclopropyl.

"Haloalkyl" refers to alkyl groups having from 1 to 5 halo groups. Preferably, such groups have from 1 to 3 halo groups and 1 to 2 carbon atoms. Particularly preferred haloalkyl groups include trihalomethyl (e.g., trifluoromethyl) and trihaloethyl (e.g., 2,2,2-trifluoroeth-1-yl).

"Alkenyl" refers to straight and branched alkenyl group having from 2 to 4 carbon atomsand preferably 2 to 3 carbon atoms and having at least 1 and preferably 1 site of alkenyl unsaturation. Examples of such alkenyl groups include vinyl ($-CH=CH_2$), allyl ($-CH_2CH=CH_2$), n-propen-1-yl ($-CH=CHCH_3$), n-buten-2-yl ($-CH_2CH=CHCH_3$), and the like. Included within this term are the cis and trans isomers or mixtures of these isomers.

"Alkynyl" refers to straight and branched alkynyl group having from 2 to 4 carbon atoms and preferably 2 to 3 carbon atoms and having at least 1 and preferably 1 site of alkynyl unsaturation. Examples of such alkynyl groups include acetylenyl ($-C\equiv CH$), propargyl ($-CH_2C\equiv CH$), n-propyn-1-yl ($-CH=CHCH_3$), and the like.

Exemplary compounds of Group I include, but are not limited to:

N-[2-diethylamino-5-{N-ethyl-N-(trifluoroacetyl) amino}pyrimidin-4-yl]-L-4'-{(pyrrolidin-1-yl) carbonyloxy}phenylalanine;

N-[2-diethylamino-5-{N-ethyl-N-(iso-propylcarbonyl)amino}pyrimidin-4-yl]-L-4'-{(pyrrolidin-1-yl)carbonyloxy}phenylalanine;
N-[2-diethylamino-5-{N-ethyl-N-(t-butylcarbonyl)amino}pyrimidin-4-yl]-L-4'-{(pyrrolidin-1-yl)carbonyloxy}phenylalanine;
N-[2-diethylamino-5-{N-ethyl-N-(furan-2-ylcarbonyl)amino}pyrimidin-4-yl]-L-4'-{(pyrrolidin-1-yl)carbonyloxy}phenylalanine;
N-[2-diethylamino-5-{N-ethyl-N-(piperidin-1-ylcarbonyl)amino}pyrimidin-4-yl]-L-4'-{(pyrrolidin-1-yl)carbonyloxy}phenylalanine;
N-[2-diethylamino-5-{N-ethyl-N-(N-ethyl-N-isopropylaminocarbonyl)amino}pyrimidin-4-yl]-L-4'-{(pyrrolidin-1-yl)carbonyloxy}phenylalanine;
N-[2-diethylamino-5-{N-ethyl-N-(thien-3-ylcarbonyl)amino}pyrimidin-4-yl]-L-4'-{(pyrrolidin-1-yl)carbonyloxy}phenylalanine;
N-[2-diethylamino-5-{N-ethyl-N-(thien-2-ylcarbonyl)amino}pyrimidin-4-yl]-L-4'-{(pyrrolidin-1-yl)carbonyloxy}phenylalanine;
N-[2-diethylamino-5-{N-ethyl-N-(furan-3-ylcarbonyl)amino}pyrimidin-4-yl]-L-4'-{(pyrrolidin-1-yl)carbonyloxy}phenylalanine;
N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy}phenylalanine; and
pharmaceutically acceptable salts and esters thereof.

Group II

In another embodiment of the present invention, compounds useful as alpha-4 integrin inhibitors are described and characterized in U.S. Published Application Nos. 20040138243 (now U.S. Pat. No. 7,026,328) and 20040142954 (now U.S. Pat. No. 7,008,949), published on Jul. 15, 2004, and Jul. 22, 2004, respectively, which are hereby incorporated by reference in their entirety for all purposes, and are compounds of Formula II a pharmaceutically acceptable salt or ester of any of the foregoing:

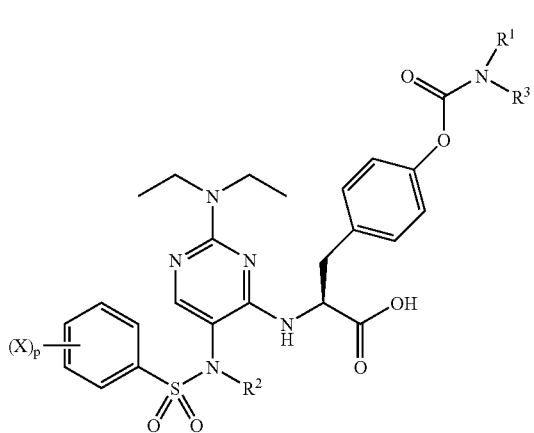

wherein the definitions of this Group II are:
each X is independently fluoro, chloro or bromo;
p is an integer from 0 to 3;
each $R^1$ and $R^3$ are independently selected from H or lower alkyl or $R^1$ and $R^3$ together with the nitrogen atom to which they are bound form an azetidinyl, pyrrolidinyl, pyrrolyl, 2,5-dihydropyrrol-1-yl, piperidinyl, or 1,2,3,6-tetrahydropyridin-1-yl ring;
$R^2$ is selected from the group consisting of lower alkyl, lower alkenyl, and lower alkylenecycloalkyl.

The terms used in Group II compounds are those defined in U.S. Published Application No. 20040138243 that include:
"Lower alkyl" refers to monovalent alkyl groups having from 1 to 5 carbon atoms including straight and branched chain alkyl groups. Groups such as methyl, ethyl, iso-propyl, n-propyl, n-butyl, iso-butyl, sec-butyl, t-butyl, n-pentyl and the like exemplify this term.
"Lower alkylene" refers to divalent alkylene groups of from 1 to 4 carbon atoms including straight and branched chain alkylene groups. This term is exemplified by groups such as methylene, ethylene, n-propylene, iso-propylene ($-CH_2CH(CH_3)-$ and $-CH(CH_3)CH_2-$) and the like.
"Lower alkenyl" refers to an alkenyl group preferably having from 2 to 6 carbon atoms and having at least 1 site and preferably only 1 site of alkenyl unsaturation (i.e., $>C=C<$). This term is exemplified by groups such as allyl, ethenyl, propenyl, butenyl, and the like.
"Lower alkynyl" refers to an alkynyl group preferably having from 2 to 6 carbon atoms and having at least 1 site and preferably only 1 site of alkynyl unsaturation (i.e., $-C\equiv C-$). This term is exemplified by groups such as acetylenyl ($-C\equiv CH$), propargyl ($-CH_2-C\equiv CH$), 3-butynyl ($-CH_2CH_2C\equiv CH_3$) and the like.
"Lower cycloalkyl" refers to cyclic alkyl groups of from 3 to 6 carbon atoms having a single cyclic ring including, by way of example, cyclopropyl, cyclobutyl, cyclopentyl and cyclohexyl.
"Lower alkylenecycloalkyl" refers to the group consisting of a lower alkylene-lower cycloalkyl, as defined herein. Such groups are exemplified by methylenecyclopropyl ($-CH_2$-cyclopropyl), ethylenecyclopropyl and the like.
Exemplary compounds of Group II include, but are not limited to:
N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine;
N-(2-[N',N'-diethylamino]-5-[N"-(4-fluorophenylsulfonyl)-N"-ethylamino]pyrimidin-4-yl)-4'-(pyrrolidin-1-ylcarbonyloxy)-L-phenylalanine;
N-(2-[N',N'-diethylamino]-5-[N"-(4-fluorophenylsulfonyl)-N"-methylamino]pyrimidin-4-yl)-4'-(pyrrolidin-1-ylcarbonyloxy)-L-phenylalanine;
N-(2-[N',N'-diethylamino]-5-[N"-(4-chlorophenylsulfonyl)-N"-methylamino]pyrimidin-4-yl)-4'-(pyrrolidin-1-ylcarbonyloxy)-L-phenylalanine;
N-(2-[N',N'-diethylamino]-5-[N"-(4-fluorophenylsulfonyl)-N"-methylamino]pyrimidin-4-yl)-4'-(piperidin-1-ylcarbonyloxy)-L-phenylalanine;
N-(2-[N',N'-diethylamino]-5-[N"-(4-fluorophenylsulfonyl)-N"-ethylamino]pyrimidin-4-yl)-4'-(piperidin-1-ylcarbonyloxy)-L-phenylalanine;
N-(2-[N',N'-diethylamino]-5-[N"-(4-fluorophenylsulfonyl)-N"-ethylamino]pyrimidin-4-yl)-4'-(azetidin-1-ylcarbonyloxy)-L-phenylalanine;
N-(2-[N',N'-diethylamino]-5-[N"-(4-fluorophenylsulfonyl)-N"-methylamino]pyrimidin-4-yl)-4'-(azetidin-1-ylcarbonyloxy)-L-phenylalanine;
N-(2-[N',N'-diethylamino]-5-[N"-(4-chlorophenylsulfonyl)-N"-methylamino]pyrimidin-4-yl)-4'-(azetidin-1-ylcarbonyloxy)-L-phenylalanine;
N-(2-[N',N'-diethylamino]-5-[N"-(4-chlorophenylsulfonyl)-N"-ethylam-ino]pyrimidin-4-yl)-4'-(azetidin-1-ylcarbonyloxy)-L-phenylalanine;
N-(2-[N',N'-diethylamino]-5-[N"-(2,4-difluorophenylsulfonyl)-N"-methylamino]pyrimidin-4-yl)-4'-(pyrrolidin-1-ylcarbonyloxy)-L-phenylalanine;

N-(2-[N',N'-diethylamino]-5-[N''-(2,4-difluorophenylsulfonyl)-N''-ethylamino]pyrimidin-4-yl)-4'-(pyrrolidin-1-ylcarbonyloxy)-L-phenylalanine;
N-(2-[N',N'-diethylamino]-5-[N''-(2,4-difluorophenylsulfonyl)-N''-methylamino]pyrimidin-4-yl)-4'-(azetidin-1-ylcarbonyloxy)-L-phenylalanine;
N-(2-[N',N'-diethylamino]-5-[N''-(2,4-difluorophenylsulfonyl)-N''-ethylamino]pyrimidin-4-yl)-4'-(azetidin-1-ylcarbonyloxy)-L-phenylalanine;
N-(2-[N',N'-diethylamino]-5-[N''-(4-fluorophenylsulfonyl)-N''-propargylamino]pyrimidin-4-yl)-4'-(pyrrolidin-1-ylcarbonyloxy)-L-phenylalanine;
N-(2-[N',N'-diethylamino]-5-[N''-(2,4-difluorophenylsulfonyl)-N''-propargylamino]pyrimidin-4-yl)-4'-(pyrrolidin-1-ylcarbonyloxy)-L-phenylalanine;
N-(2-[N',N'-diethylamino]-5-[N''-(2,4-difluorophenylsulfonyl)-N''-propargylamino]pyrimidin-4-yl)-4'-(azetidin-1-ylcarbonyloxy)-L-phenylalanine;
N-(2-[N',N'-diethylamino]-5-[N''-(4-fluorophenylsulfonyl)-N''-propargylamino]pyrimidin-4-yl)-4'-(azetidin-1-ylcarbonyloxy)-L-phenylalanine;
N-(2-[N',N'-diethylamino]-5-[N''-(4-chlorophenylsulfonyl)-N''-propargylamino]pyrimidin-4-yl)-4'-(pyrrolidin-1-ylcarbonyloxy)-L-phenylalanine;
2-{2-diethylamino-5-[(4-chlorobenzenesulfonyl)methylamino]-pyrimidin-4-ylamino}-3-(4-dimethylcarbamoyloxyphenyl)propionic acid;
2-{2-diethylamino-5-[(4-fluorobenzenesulfonyl)methylamino]-pyrimidin-4-ylamino}-3-(4-dimethylcarbamoyloxyphenyl)propionic acid;
2-{2-diethylamino-5-[(3,4-difluorobenzenesulfonyl)methylamino]-pyrimidin-4-ylamino}-3-(4-dimethylcarbamoyloxyphenyl)propionic acid;
2-{2-diethylamino-5-[(3,4-dichlorobenzenesulfonyl)methylamino]-pyrimidin-4-ylamino}-3-(4-dimethylcarbamoyloxyphenyl)propionic acid;
2-{2-diethylamino-5-[(benzenesulfonyl)methylamino]-pyrimidin-4-ylamino}-3-(4-dimethylcarbamoyloxyphenyl)propionic acid;
2-{2-diethylamino-5-[(2-fluorobenzenesulfonyl)methylamino]-pyrimidin-4-ylamino}-3-(4-dimethylcarbamoyloxyphenyl)propionic acid;
2-{2-diethylamino-5-[(3-fluorobenzenesulfonyl)methylamino]-pyrimidin-4-ylamino}-3-(4-dimethylcarbamoyloxyphenyl)propionic acid;
2-{2-diethylamino-5-[(4-fluorobenzenesulfonyl)isopropylamino]-pyrimidin-4-ylamino}-3-(4-dimethylcarbamoyloxyphenyl)propionic acid;
2-{2-diethylamino-5-[(4-fluorobenzenesulfonyl)ethylamino]-pyrimidin-4-ylamino}-3-(4-dimethylcarbamoyloxyphenyl)propionic acid;
2-{2-diethylamino-5-[(3,4-difluorobenzenesulfonyl)isopropylamino]-pyrimidin-4-ylamino}-3-(4-dimethylcarbamoyloxyphenyl)propionic acid;
2-{2-diethylamino-5-[(4-chlorobenzenesulfonyl)isopropylamino]-pyrimidin-4-ylamino}-3-(4-dimethylcarbamoyloxyphenyl)propionic acid;
2-{2-diethylamino-5-[(3,4-difluorobenzenesulfonyl)ethylamino]-pyrimidin-4-ylamino}-3-(4-dimethylcarbamoyloxyphenyl)propionic acid;
2-{2-diethylamino-5-[(4-chlorobenzenesulfonyl)ethylamino]-pyrimidin-4-ylamino}-3-(4-dimethylcarbamoyloxyphenyl)propionic acid;
2-{2-diethylamino-5-[(4-fluorobenzenesulfonyl)cylclopropylmethyl-amino]pyrimidin-4-ylamino}-3-(4-dimethylcarbamoyloxyphenyl)propionic acid;
2-{2-diethylamino-5-[(3,5-difluorobenzenesulfonyl)methylamino]-pyrimidin-4-ylamino}-3-(4-dimethylcarbamoyloxyphenyl)propionic acid 2-{2-diethylamino-5-[(3,5-difluorobenzenesulfonyl)ethylamino]-pyrimidin-4-ylamino}-3-(4-dimethylcarbamoyloxyphenyl)propionic acid;
2-{2-diethylamino-5-[(2,4-difluorobenzenesulfonyl)methylamino]-pyrimidin-4-ylamino}-3-(4-dimethylcarbamoyloxyphenyl)propionic acid;
2-{2-diethylamino-5-[(2,4-difluorobenzenesulfonyl)ethylamino]-pyrimidin-4-ylamino}-3-(4-dimethylcarbamoyloxyphenyl)propionic acid;
2-{2-diethylamino-5-[(3,5-dichlorobenzenesulfonyl)methylamino]-pyrimidin-4-ylamino}-3-(4-dimethylcarbamoyloxyphenyl)propionic acid;
2-{2-diethylamino-5-[(3,5-dichlorobenzenesulfonyl)ethylamino]-pyrimidin-4-ylamino}-3-(4-dimethylcarbamoyloxyphenyl)propionic acid;
2-{2-diethylamino-5-[(4-fluorobenzenesulfonyl)-n-propylamino]-pyrimidin-4-ylamino}-3-(4-dimethylcarbamoyloxyphenyl)propionic acid;
2-{2-diethylamino-5-[(4-fluorobenzenesulfonyl)allylamino]-pyrimidin-4-ylamino}-3-(4-dimethylcarbamoyloxyphenyl)propionic acid;
2-{2-diethylamino-5-[(4-fluorobenzenesulfonyl)isobutylamino]-pyrimidin-4-ylamino}-3-(4-dimethylcarbamoyloxyphenyl)propionic acid 2-{2-diethylamino-5-[(4-fluorobenzenesulfonyl)-n-butylamino]-pyrimidin-4-ylamino}-3-(4-dimethylcarbamoyloxyphenyl)propionic acid;
2-{2-diethylamino-5-[(2,5-difluorobenzenesulfonyl)methylamino]-pyrimidin-4-ylamino}-3-(4-dimethylcarbamoyloxyphenyl)propionic acid;
2-{2-diethylamino-5-[(2,3-difluorobenzenesulfonyl)ethylamino]-pyrimidin-4-ylamino}-3-(4-dimethylcarbamoyloxyphenyl)propionic acid;
2-{2-Diethylamino-5-[(4-fluorobenzenesulfonyl)-(2-trisfluoroethyl)-amino]pyrimidin-4-ylamino}-3-(4-dimethylcarbamoyloxyphenyl)propionic acid; and
pharmaceutically acceptable salts and esters thereof.

Group III

In yet another embodiment of the present invention, compounds useful as alpha-4 integrin inhibitors are described and characterized in U.S. Published Application No. 20030176498, published on Sep. 18, 2003 (now U.S. Pat. No. 7,026,501), which is hereby incorporated by reference in its entirety for all purposes, and are compounds of Formula III, a pharmaceutically acceptable salt or ester of any of the foregoing,

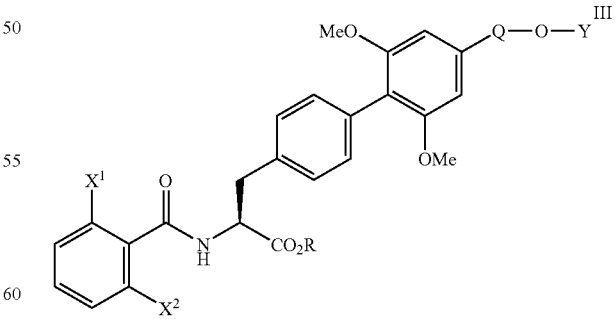

wherein: $X^1$ is a halogen atom; $X^2$ is a halogen atom; Q is a —$CH_2$— group or a —$(CH_2)2$— group; Y is a C1-6 alkyl group; and $CO_2R$ is a carboxyl group which may be esterified.

The terms used in Group III compounds are those defined in U.S. Published Application No. 20030176498 that include:

a halogen atom means chlorine atom, fluorine atom, bromine atom or iodine atom; and C1-6 alkyl group means a straight, branched or cycloalkyl group having 1 to 6 carbon atoms, preferably 1 to 4 carbon atoms, such as methyl, ethyl, n-propyl, n-butyl, isopropyl, cyclopropyl, tert-butyl and the like.

Exemplary compounds of Group III include, but are not limited to:

N-(2,6-Difluorobenzoyl)-4-(2,6-dimethoxy-4-ethoxymethylphenyl)-L-phenylalanine;

N-(2-Chloro-6-fluorobenzoyl)-4-(2,6-dimethoxy-4-ethoxymethylphenyl)-L-phenylalanine;

N-(2-Chloro-6-fluorobenzoyl)-4-(2,6-dimethoxy-4-methoxymethylphenyl)-L-phenylalanine;

N-(2,6-Difluorobenzoyl)-4-(2,6-dimethoxy-4-methoxymethylphenyl)-L-phenylalanine;

or a C1-6 alkyl ester thereof;

and pharmaceutically acceptable salts thereof.

Group IV

In another embodiment of the present invention, a compound useful as an alpha-4 integrin inhibitor is described and characterized among other compounds in U.S. Pat. No. 6,229,011, issued on May 8, 2001, which is hereby incorporated by reference in its entirety for all purposes, and is the compound of Formula IV, a pharmaceutically acceptable salt or ester of any of the foregoing:

IV

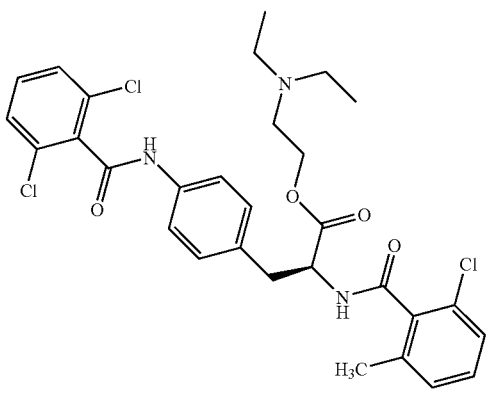

Group V

In another embodiment of the present invention, compounds useful as alpha-4 integrin inhibitors are described and characterized in U.S. Provisional Application No. 60/777,595, filed on Feb. 27, 2006, to Andrei Konradi et al., the disclosure of which is hereby incorporated by reference in its entirety for all purposes, and includes compounds of Formula V, a pharmaceutically acceptable salt or ester of any of the foregoing:

V

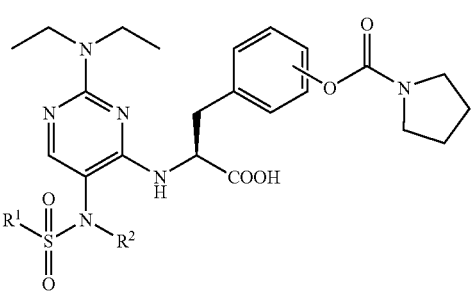

wherein:

$R^1$ is selected from the group consisting of $C_1$ to $C_4$ alkyl and $C_1$ to $C_4$ haloalkyl; and $R^2$ is selected from the group consisting of $C_1$ to $C_4$ alkyl, $C_2$ to $C_4$ alkenyl, $C_2$ to $C_4$ alkynyl, $C_3$-$C_6$ cycloalkyl and benzyl;

The terms used in the Group V compounds are those defined that include:

"Alkyl" refers to monovalent straight and branched hydrocarbyl groups having from 1 to 4 carbon atoms and preferably 1 to 3 carbon atoms. This term is exemplified by groups such as methyl, ethyl, n-propyl, iso-propyl, n-butyl, iso-butyl, sec-butyl, and t-butyl.

"Alkenyl" refers to straight or branched monovalent hydrocarbyl groups from 2 to 4 carbon atoms and preferably 2 to 3 carbon atoms and having at least 1 and preferably 1 site of vinyl (>C=C<) unsaturation. Examples of such alkenyl groups include vinyl (—CH=CH$_2$), allyl (—CH$_2$CH=CH$_2$), n-propen-1-yl (—CH=CHCH$_3$), n-buten-2-yl (—CH$_2$CH=CHCH$_3$), and the like. Included within this term are the cis and trans isomers or mixtures of these isomers.

"Alkynyl" refers to straight or branched monovalent hydrocarbyl groups having from 2 to 4 carbon atoms and preferably 2 to 3 carbon atoms and having at least 1 and preferably 1 site of acetylenic —C≡C— unsaturation. Examples of such alkynyl groups include acetylenyl (—C≡CH), propargyl (—CH$_2$C≡CH), n-propyn-1-yl (—CH=CHCH$_3$), and the like.

"Halo" or "halogen" refers to fluoro, chloro, bromo and iodo and preferably is either fluoro or chloro.

"Haloalkyl" refers to alkyl groups having from 1 to 5 halo groups. Preferably, such groups have from 1 to 3 halo groups and 1 to 2 carbon atoms. Particularly preferred haloalkyl groups include trihalomethyl (e.g., trifluoromethyl) and trihaloethyl (e.g., 2,2,2-trifluoroeth-1-yl).

Exemplary compounds of Group V include, but are not limited to:

N-[2-diethylamino-5-(N-ethyl-trifluorosulfonamido)pyrimidin-4-yl]-L-4'-{(pyrrolidin-1-yl)carbonyloxy}phenylalanine;

N-[2-diethylamino-5-(N-isopropyl-methylsulfonamdo)pyrimidin-4-yl]-L-4'-{(pyrrolidin-1-yl)carbonyloxy}phenylalanine;

N-[2-diethylamino-5-{N-cycolhexyl-N-(methylsulfonamido)pyrimidin-4-yl]-L-4'-{(pyrrolidin-1-yl)carbonyloxy}phenylalanine;

N-[2-diethylamino-5-{N-methyl-methylsulfonamido}pyrimidin-4-yl]-L-4'-{(pyrrolidin-1-yl)carbonyloxy}phenylalanine;

N-[2-diethylamino-5-{N-propargyl-methylsulfonamido}pyrimidin-4-yl]-L-4'-{(pyrrolidin-1-yl)carbonyloxy)}phenylalanine;

N-[2-diethylamino-5-{N-ethyl-methylsulfonamido)pyrimi-
din-4-yl]-L-4'-{(pyrrolidin-1-yl)
carbonyloxy}phenylalanine;
N-[2-diethylamino-5-{N-benzyl-methylsulfonamido)pyri-
midin-4-yl]-L-4'-{(pyrrolidin-1-yl)
carbonyloxy}phenylalanine; and
N-[2-diethylamino-5-{N-allyl-methylsulfonamido)pyrimi-
din-4-yl]-L-4'-{(pyrrolidin-1-yl)
carbonyloxy}phenylalanine
and pharmaceutically acceptable salts and esters thereof.

Group VI

In another embodiment, compounds useful as alpha-4 integrin inhibitors are described and characterized in U.S. Published Application No. 20030027771, published on Feb. 6, 2003 (now U.S. Pat. No. 7,101,855), which is hereby incorporated by reference in its entirety for all purposes, and includes compounds of Formula VI, a pharmaceutically acceptable salt or ester of any of the foregoing:

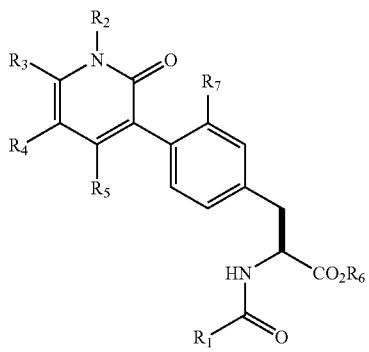

VI wherein $R_1$ is a group of the formula Y-1

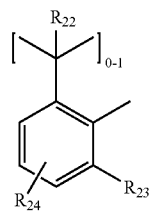

Y-1 wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluoro lower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen;

or $R_1$ is a group of the formula Y-2, which is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoro lower alkyl, or aryl and at least one of said substituted atoms is adjacent to the carbon atom bonded to the amide carbonyl;

or $R_1$ is a group of the formula Y-3 which is a 3-7 membered ring of the formula:

Y-3 wherein $R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or $R_{28}$ and $R_{29}$, taken together with the attached nitrogen atom, form a 4, 5 or 6-membered saturated heterocyclic ring optionally containing one additional heteroatom selected from O, S, and N—$R_{40}$, Q is —$(CH_2)_f$—O—, —$(CH_2)_f S$—, —$(CH_2)_f N(R_{27})$—, —$(CH_2)_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3; $R_2$ is hydrogen, lower alkyl, substituted lower alkyl, aryl, or aryl lower alkyl;

$R_3$ is hydrogen, halogen, lower alkyl, trifluoromethyl, or aryl; $R_4$ is hydrogen, halogen, lower alkyl, or aryl;

$R_5$ is hydrogen, lower alkyl, lower alkoxy, or trifluoromethyl, or OH; $R_6$ is hydrogen, lower alkyl, lower alkylcarbonyloxy lower alkyl, or $R_6$ is a group of formula P-3:

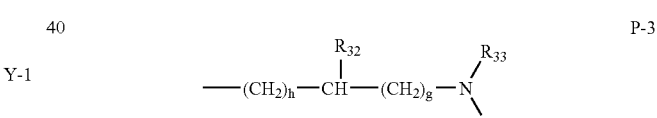

P-3 wherein: $R_{32}$ is hydrogen or lower alkyl; $R_{33}$ is hydrogen, lower alkyl, aryl; $R_{34}$ is hydrogen or lower alkyl;
h is an integer from 0 to 2;
g is an integer from 0 to 2; the sum of h and g is 1 to 3;
or $R_6$ is a group of formula P-3:

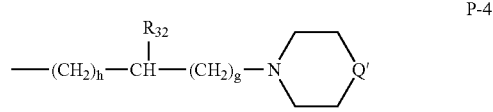

P-4 wherein: $R_{32}$, g, and h are as previously defined; Q' is O, S, —$(CH_2)j$-, or a group of the formula N—$R_{35}$; wherein $R_{35}$ is hydrogen, lower alkyl, lower alkanoyl, lower alkoxycarbonyl; j is 0, 1 or 2; and $R_7$ is hydrogen, chloro, lower alkoxy, or lower alkyl.

As used in this specification, the term "halogen" refers to any of the four halogens, bromine, chlorine, fluorine, and iodine unless indicated otherwise. Preferred halogens are bromine, fluorine, and chlorine.

The term "lower alkyl", alone or in combination, refers to a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Also, as used herein "lower alkyl" may be groups which are unsubstituted or substituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl, and amino or mono- or di-lower alkylamino. Examples of substituted lower alkyl groups include 2-hydroxyethyl, 3-oxobutyl, cyanomethyl, and 2-nitropropyl. Although this invention is specifically directed to the substituted lower alkyl group trifluoromethyl at positions $R_3$, $R_5$, $R_{22}$ and $R_{23}$, pentafluoroethyl is also contemplated at these positions.

The term "cycloalkyl" (or lower cycloalkyl) refers to an unsubstituted or substituted 3- to 7-membered carbacyclic ring. Substituents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino. The term "lower alkenyl" refers to an alkylene group having from 2 to 10 carbon atoms with a double bond located between any two adjacent carbon atoms.

The term "lower alkoxy" refers to a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" refers to a lower alkyl group bonded to the rest of the molecule through a divalent sulfur atom, for example, a methyl mercapto or a isopropyl mercapto group. The term "lower alkylsulfinyl" refers to a lower alkyl group as defined above bound to the rest of the molecule through the sulfur atom in the sulfinyl group. The term "lower alkyl sulfonyl" refers to a lower alkyl group as defined above bound to the rest of the molecule through the sulfur atom in the sulfonyl group.

The term "aryl" refers to a mono- or bicylic aromatic group, such as phenyl or naphthyl, which is unsubstituted or substituted by conventional substituent groups. Exemplary substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoro lower alkyl, alkanoyl, aroyl, aryl alkynyl, lower alkynyl and lower alkanoylamino. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "arylalkyl" refers to a lower alkyl group as hereinbefore defined in which one or more hydrogen atoms is/are replaced by an aryl or heteroaryl group as herein defined. Any conventional aralkyl may be used in accordance with this invention, such as benzyl and the like.

The term "heteroaryl" refers to an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of heteroaryl rings are pyridine, benzimidazole, indole, imidazole, thiophene, isoquinoline, quinzoline and the like. Substituents as defined above for "aryl" are included in the definition of heteroaryl.

The term "lower alkoxycarbonyl" refers to a lower alkoxy group bonded via a carbonyl group. Examples of alkoxycarbonyl groups are ethoxycarbonyl and the like.

The term "lower alkylcarbonyloxy" refers to lower alkylcarbonyloxy groups bonded via an oxygen atom, for example an acetoxy group. This has the same meaning as the term "acyloxy".

The term "lower alkanoyl" refers to lower alkyl groups bonded via a carbonyl group and embraces in the sense of the foregoing definition groups such as acetyl, propionyl and the like. The term "perfluoro lower alkanoyl" means a perfluoro lower alkyl group (a substituted lower alkyl group where all of the hydrogens are substituted by fluoro, preferably trifluoromethyl or pentafluoroethyl) bonded to the rest of the molecule via a carbonyl group. The term "perfluoro lower alkanoylamino" refers to a perfluoro lower alkanoyl group bonded to the rest of the molecule via an amino group.

The term "lower alkylcarbonylamino" refers to lower alkylcarbonyl groups bonded to the rest of the molecule via a nitrogen atom, such as acetylamino. The term lower alkylaminocarbonyl" refers to lower alkylamino groups bonded to the rest of the molecule via a carbonyl group. The term "arylaminocarbonyl" refers to aryl groups bonded to an amino group further bonded to the rest of the molecule via a carbonyl group.

The term "aroyl" refers to a mono- or bicyclic aryl or heteroaryl group bonded to the rest of the molecule via a carbonyl group. Examples of aroyl groups are benzoyl, 3-cyanobenzoyl, 2-naphthoyl, nicotinoyl, and the like.

Exemplary compounds of this Group VI include, but are not limited to:

N-[(2,6-dichlorophenyl)carbonyl]-4-[1,-6-dimethyl-4-(trifluoromethyl)-2-oxo-3-pyridinyl]-L-phenylalanine ethyl ester;

N-[(2,6-dichlorophenyl)carbonyl]-4-[1,-4-dimethyl-6-(trifluoromethyl)-2-oxo-3-pyridinyl]-L-phenylalanine ethyl ester;

N-[(2-chloro-6-methylphenyl)carbonyl]-4-[1,6-dimethyl-4-(trifluoromethyl)-2-oxo-3-pyridinyl]-L-phenylalanine ethyl ester;

N-[(2-chloro-6-methylphenyl)carbonyl]-4-[1,4-dimethyl-6-(trifluoromethyl)-2-oxo-3-pyridinyl]-L-phenylalanine ethyl ester;

N-[(2,6-dichlorophenyl)carbonyl]-4-[1,-6-dimethyl-4-(trifluoromethyl)-2-oxo-3-pyridinyl]-L-phenylalanine 1-(acetoxy)ethyl ester;

N-[(2,6-dichlorophenyl)carbonyl]-4-[1,-4-dimethyl-6-(trifluoromethyl)-2-oxo-3-pyridinyl]-L-phenylalanine 1-(acetoxy)ethyl ester;

N-[(2-chloro-6-methylphenyl)carbonyl]-4-[1,6-dimethyl-4-(trifluoromethyl)-2-oxo-3-pyridinyl]-L-phenylalanine 1-(acetoxy)ethyl ester.)

N-[(2-chloro-6-methylphenyl)carbonyl]-4-[1,4-dimethyl-6-(trifluoromethyl)-2-oxo-3-pyridinyl]-L-phenylalanine 1-(acetoxy)ethyl ester; N-[(2,6-dichlorophenyl)carbonyl]-4-[1,-6-dimethyl-4-(trifluoromethyl)-2-oxo-3-pyridinyl]-L-phenylalanine 2-[(N,N-diethyl)amino]ethyl ester;

N-[(2,6-dichlorophenyl)carbonyl]-4-[1,-4-dimethyl-6-(trifluoromethyl)-2-oxo-3-pyridinyl]-L-phenylalanine 2-[(N,N-diethyl)amino]ethyl ester;

N-[(2-chloro-6-methylphenyl)carbonyl]-4-[1,6-dimethyl-4-(trifluoromethyl)-2-oxo-3-pyridinyl]-L-phenylalanine 2-[(N,N-diethyl)amino]ethyl ester;

N-[(2-chloro-6-methylphenyl)carbonyl]-4-[1,4-dimethyl-6-(trifluoromethyl)-2-oxo-3-pyridinyl]-L-phenylalanine 2-[(N,N-diethyl)amino]ethyl ester. N-[(2-chloro-6-methylphenyl)carbonyl]-4-(5-chloro-1-methyl-2-oxo-3-pyridinyl)-L-phenylalanine;

N-[(2-chloro-6-methylphenyl)carbonyl]-4-(1-methyl-2-oxo-3-pyridinyl)-L-phenylalanine;

N-[(2-chloro-6-methylphenyl)carbonyl]-4-(1,4-dimethyl-2-oxo-3-pyridinyl)-L-phenylalanine;

N-[(2,6-dichlorophenyl)carbonyl]-4-(1,-4-dimethyl-2-oxo-3-pyridinyl)-L-phenylalanine;

N-[(2-bromo-5-methoxyphenyl)carbonyl]-4-(1-methyl-2-oxo-3-pyridinyl)-L-phenylalanine;

N-[(2-bromo-5-methoxyphenyl)carbonyl]-4-(5-bromo-1-methyl-2-oxo-3-pyridinyl)-L-phenylalanine;

4-(5-chloro-1-methyl-2-oxo-3-pyridinyl-)-N-[[1-(2-methoxyethyl)cyclopentyl]carbonyl]-L-phenylalanine;

4-(1-Benzyl-5-chloro-2-oxo-3-pyridinyl-)-N-[(2-chloro-6-methylphenyl)carbonyl]-L-phenylalanine;

4-(1-Benzyl-5-chloro-2-oxo-3-pyridinyl-)-N-[[1-(2-methoxyethyl)cyclopentyl]carbonyl]-L-phenylalanine;

N-[[1-(2-methoxyethyl)cyclopentyl]carbonyl]-4-[1,6-dimethyl-4-(trifluoromethyl)-2-oxo-3-pyridinyl]-L-phenylalanine;

N-[(2,6-dichlorophenyl)carbonyl]-4-[1,6-dimethyl-4-(trifluoromethyl)-2-oxo-3-pyridinyl]-L-phenylalanine ethyl ester;

N-[(2,6-dichlorophenyl)carbonyl]-4-[1,4-dimethyl-6-(trifluoromethyl)-2-oxo-3-pyridinyl]-L-phenylalanine ethyl ester;

N-[(2-chloro-6-methylphenyl)carbonyl]-4-[1,6-dimethyl-4-(trifluoromethyl)-2-oxo-3-pyridinyl]-L-phenylalanine ethyl ester;

N-[(2-chloro-6-methylphenyl)carbonyl]-4-[1,4-dimethyl-6-(trifluoromethyl)-2-oxo-3-pyridinyl]-L-phenylalanine ethyl ester;

N-[(2,6-dichlorophenyl)carbonyl]-4-[1,6-dimethyl-4-(trifluoromethyl)-2-oxo-3-pyridinyl]-L-phenylalanine 1-(acetoxy)ethyl ester;

N-[(2,6-dichlorophenyl)carbonyl]-4-[1,4-dimethyl-6-(trifluoromethyl)-2-oxo-3-pyridinyl]-L-phenylalanine 1-(acetoxy)ethyl ester;

N-[(2-chloro-6-methylphenyl)carbonyl]-4-[1,6-dimethyl-4-(trifluoromethyl)-2-oxo-3-pyridinyl]-L-phenylalanine 1-(acetoxy)ethyl ester;

N-[(2-chloro-6-methylphenyl)carbonyl]-4-[1,4-dimethyl-6-(trifluoromethyl)-2-oxo-3-pyridinyl]-L-phenylalanine 1-(acetoxy)ethyl ester;

N-[(2,6-dichlorophenyl)carbonyl]-4-[1,6-dimethyl-4-(trifluoromethyl)-2-oxo-3-pyridinyl]-L-phenylalanine 2-[(N,N-diethyl)amino]ethyl ester;

N-[(2,6-dichlorophenyl)carbonyl]-4-[1,4-dimethyl-6-(trifluoromethyl)-2-oxo-3-pyridinyl]-L-phenylalanine 2-[(N,N-diethyl)amino]ethyl ester;

N-[(2-chloro-6-methylphenyl)carbonyl]-4-[1,6-dimethyl-4-(trifluoromethyl)-2-oxo-3-pyridinyl]-L-phenylalanine 2-[(N,N-diethyl)amino]ethyl ester;

N-[(2-chloro-6-methylphenyl)carbonyl]-4-[1,4-dimethyl-6-(trifluoromethyl)-2-oxo-3-pyridinyl]-L-phenylalanine 2-[(N,N-diethyl)amino]ethyl ester;

N-[(2-chloro-6-methylphenyl)carbonyl]-4-(5-chloro-1-methyl-2-oxo-3-pyridinyl)-L-phenylalanine;

N-[(2-chloro-6-methylphenyl)carbonyl]-4-(1-methyl-2-oxo-3-pyridinyl)-L-phenylalanine;

N-[(2-chloro-6-methylphenyl)carbonyl]-4-(1,4-dimethyl-2-oxo-3-pyridinyl)-L-phenylalanine;

N-[(2,6-dichlorophenyl)carbonyl]-4-(1,4-dimethyl-2-oxo-3-pyridinyl)-L-phenylalanine;

N-[(2-bromo-5-methoxyphenyl)carbonyl]-4-(1-methyl-2-oxo-3-pyridinyl)-L-phenylalanine;

N-[(2-bromo-5-methoxyphenyl)carbonyl]-4-(5-bromo-1-methyl-2-oxo-3-pyridinyl)-L-phenylalanine;

4-(5-chloro-1-methyl-2-oxo-3-pyridinyl)-N-[[1-(2-methoxyethyl)cyclopentyl]carbonyl]-L-phenylalanine;

4-(1-Benzyl-5-chloro-2-oxo-3-pyridinyl)-N-[(2-chloro-6-methylphenyl)carbonyl]-L-phenylalanine; and 4-(1-Benzyl-5-chloro-2-oxo-3-pyridinyl)-N-[[1-(2-methoxyethyl)cyclopentyl]carbonyl]-L-phenylalanine.

Group VII

In another embodiment of the present invention, compounds useful as alpha-4 integrin inhibitors are described and characterized in U.S. Published Application No. 20060013799, published on Jan. 19, 2006, which is hereby incorporated by reference in its entirety for all purposes, and discloses small molecule alpha-4 inhibitors modified by conjugation to polyethylene glycol (PEG) molecules having molecular weights of from about 30 kDa to about 70 kDa. The PEG molecules having three or more valences available for bonding to molecules of alpha-4 inhibitors. Conjugates of this Group VII are compounds of the formula VII:

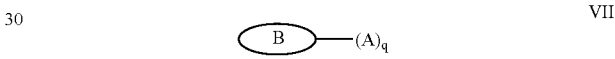

wherein B is a bio-compatible polymer moiety optionally covalently attached to a branched-arm hub molecule;
q is from about 2 to about 100;
A at each occurrence is independently a compound of formula IIa

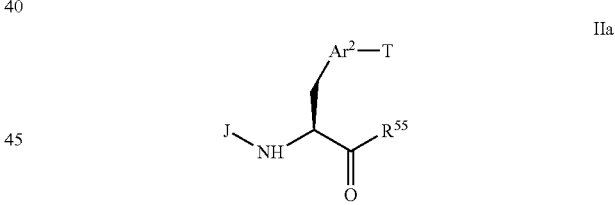

and a pharmaceutically acceptable salt of any of the foregoing, wherein
J is selected from:
a) a group of formula (a):

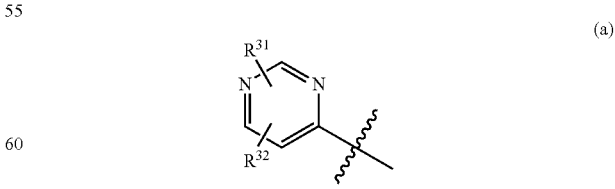

wherein $R^{31}$ is a covalent bond to the polymer moiety which optionally comprises a linker, or $R^{31}$ is —H, $R^{31'}$, —NH$_2$, —NHR$^{31'}$ or —N(R$^{31'}$)$_2$, —NC$_3$-C$_6$cyclic, —OR$^{31'}$, —SR$^{31'}$, wherein each $R^{31'}$ is independently an optionally substituted straight or branched $C_1$-$C_6$alkyl, optionally substituted $C_3$-$C_6$cycloalkyl, optionally substituted aryl, optionally substituted heteroaryl, and $R^{32}$ is a covalent bond to the polymer moiety which optionally comprises a linker, or $R^{32}$ is —H, —$NO_2$, haloalkyl or the group —$N(MR^{41})R^{42}$ wherein M is a covalent bond, —C(O)— or —$SO_2$—, $R^{41}$ is $R^{41'}$, $N(R^{41'})_2$, or —$OR^{41'}$, wherein each $R^{41'}$ is independently hydrogen, an optionally substituted straight or branched $C_1$-$C_6$alkyl, optionally substituted cycloalkyl, optionally substituted aryl, optionally substituted heterocyclic or an optionally substituted heteroaryl, wherein optional substitutions are halide, $C_1$-$C_6$alkyl, or —$OC_1$-$C_6$alkyl, and $R^{42}$ is hydrogen or $R^{41'}$; and b) a group of formula (b):

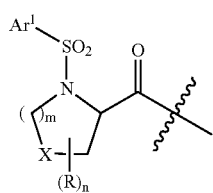

(b)

wherein R is selected from the group consisting of a covalent bond to the polymer moiety, amino, hydroxyl, substituted amino, alkyl, alkyloxy, aryloxy, heteroaryloxy, heterocyclyloxy, thiol, arylthio, heteroarylthio, heterocyclylthio and substituted alkyl wherein each amino, substituted amino, alkyl and substituted alkyl is optionally covalently bound to the polymer moiety wherein, in each case, the polymer moiety optionally comprises a linker which covalently links the polymer moiety;

$Ar^1$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to $Ar^1$;

X is selected from the group consisting of —$NR^1$—, —O—, —S—, —SO—, —$SO_2$ and optionally substituted —$CH_2$— where $R^1$ is selected from the group consisting of hydrogen and alkyl;

m is an integer equal to 0, 1 or 2;

n is an integer equal to 0, 1 or 2; and $Ar^2$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to $Ar^2$ T is selected from:

a) a group of formula (c)

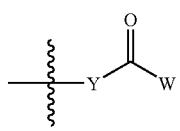

(c)

wherein Y is selected from the group consisting of —O— and —$NR^1$— wherein $R^1$ is selected from the group consisting of hydrogen and alkyl;

W is selected from the group consisting of a covalent bond to a polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;

b) a group of formula (d)

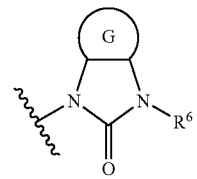

(d)

wherein G is an optionally substituted aryl or optionally substituted heteroaryl 5 or 6 membered ring containing 0 to 3 nitrogens, wherein said aryl or heteroary optionally further comprises a covalent bond to a polymer moiety which optionally comprises a linker;

$R^6$ is a covalent bond to a polymer moiety which optionally comprises a linker, or $R^6$ is —H, alkyl, substituted alkyl, or —$CH_2C(O)R^{17}$, wherein $R^{17}$ is —OH, —$OR^{18}$, or —$NHR^{18}$, wherein $R^{18}$ is alkyl, substituted alkyl, aryl or substituted aryl;

$R^{55}$ is selected from the group consisting of amino, substituted amino, alkoxy, substituted alkoxy, cycloalkoxy, substituted cycloalkoxy, aryloxy and substituted aryloxy, and —OH;

provided that:

A. at least one of R, $Ar^1$, $Ar^2$, and T contains a covalent bond to the polymer moiety;

B. when R is covalently bound to the polymer moiety, n is one and X is not —O—, —S—, —SO—, or —$SO_2$—;

C. when X is —O— or —$NR^1$—, then m is two; and

D. the conjugate of formula VII has a molecular weight of no more than 100,000.

A linker that covalently links the polyalkylene oxide moieties of the PEG polymer one to another is referred to as a "branched-arm hub", or "branched-arm hub molecule". Branched-arm hubs are molecules that covalently bond two or more polyalkylene oxide chains to them, providing divalent or higher valency polymer moieties for conjugation with the active compound. Non-limiting examples of such hub molecules are glycerol (1,2,3-propanetriol), pentaerythritol, lysine, 1,2,4-benzenetriol, glucose (in its pyranose form), ethylenediamine tetraacetic acid, amino acids, 3- or 4-aminosalicylic acid, 1,3-diamino-2-hydroxypropane, glucosamine, and sialic acid. Other terms and definitions are as provided in US published application 20060013799.

Exemplary compounds of Group VII include, but are not limited to:

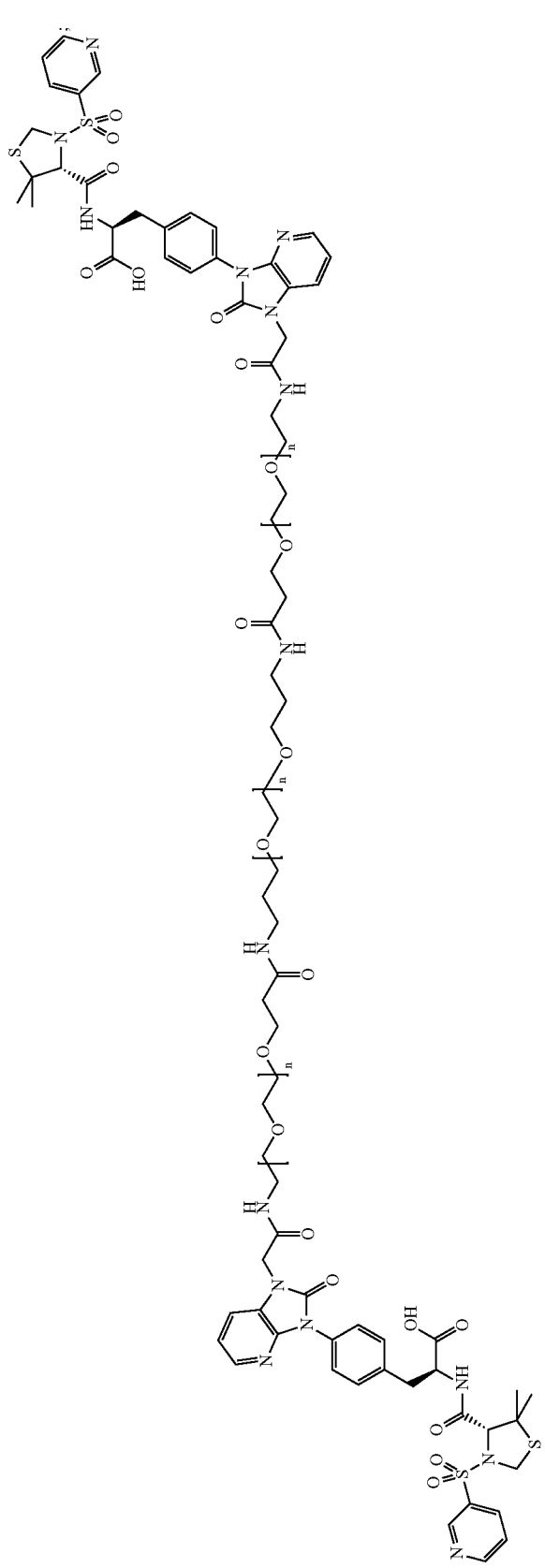
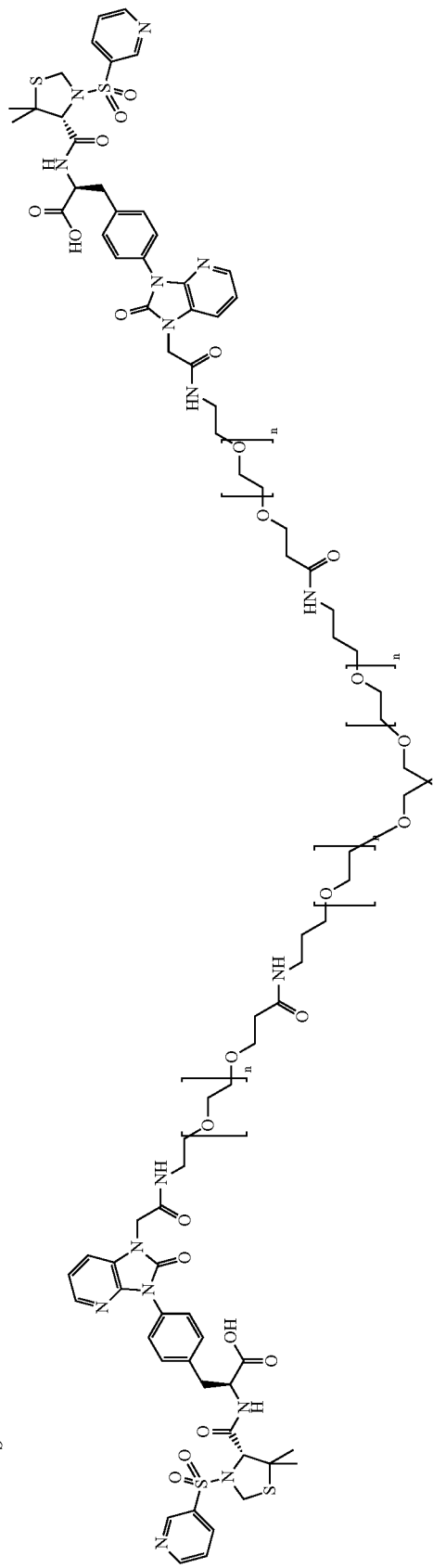

-continued
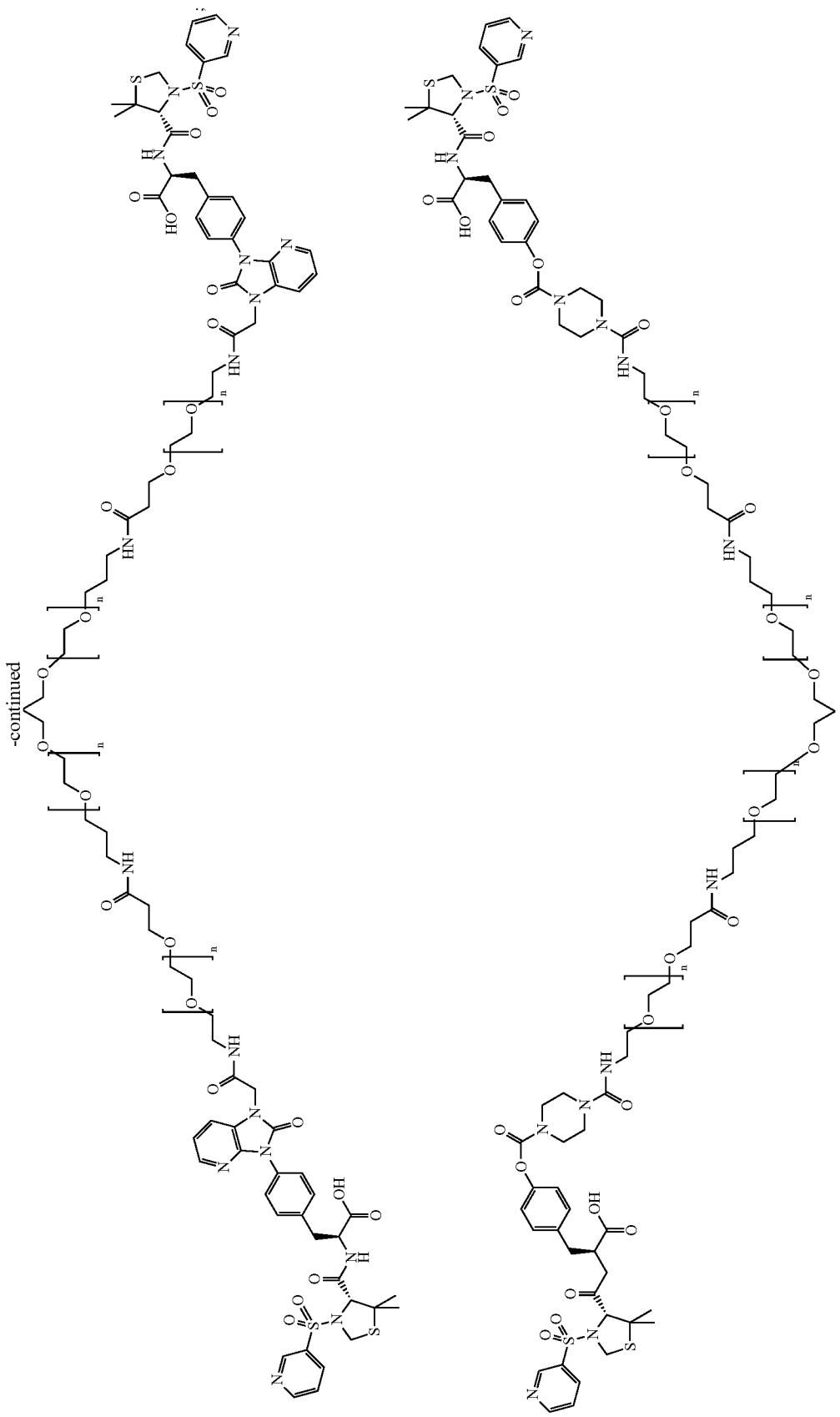

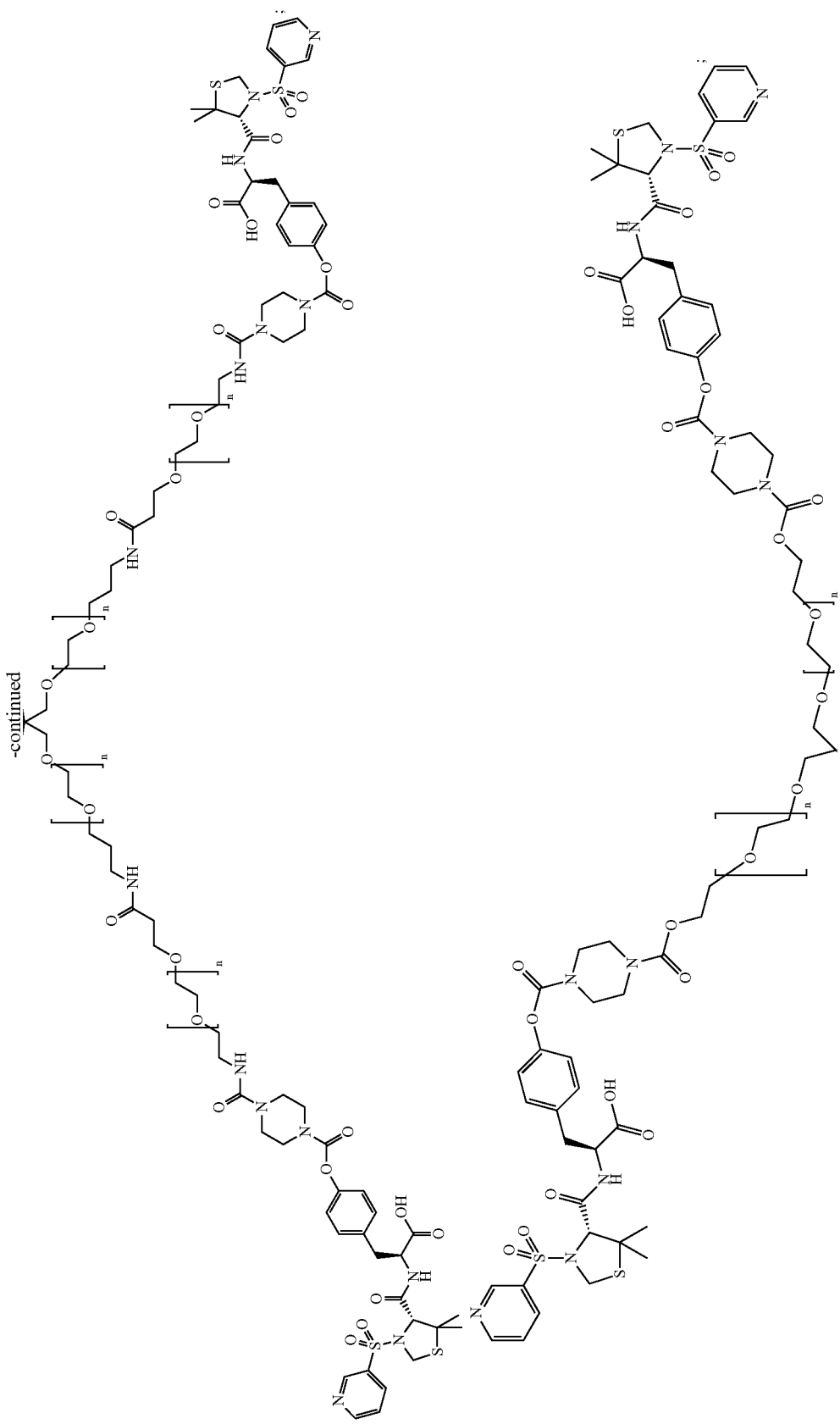

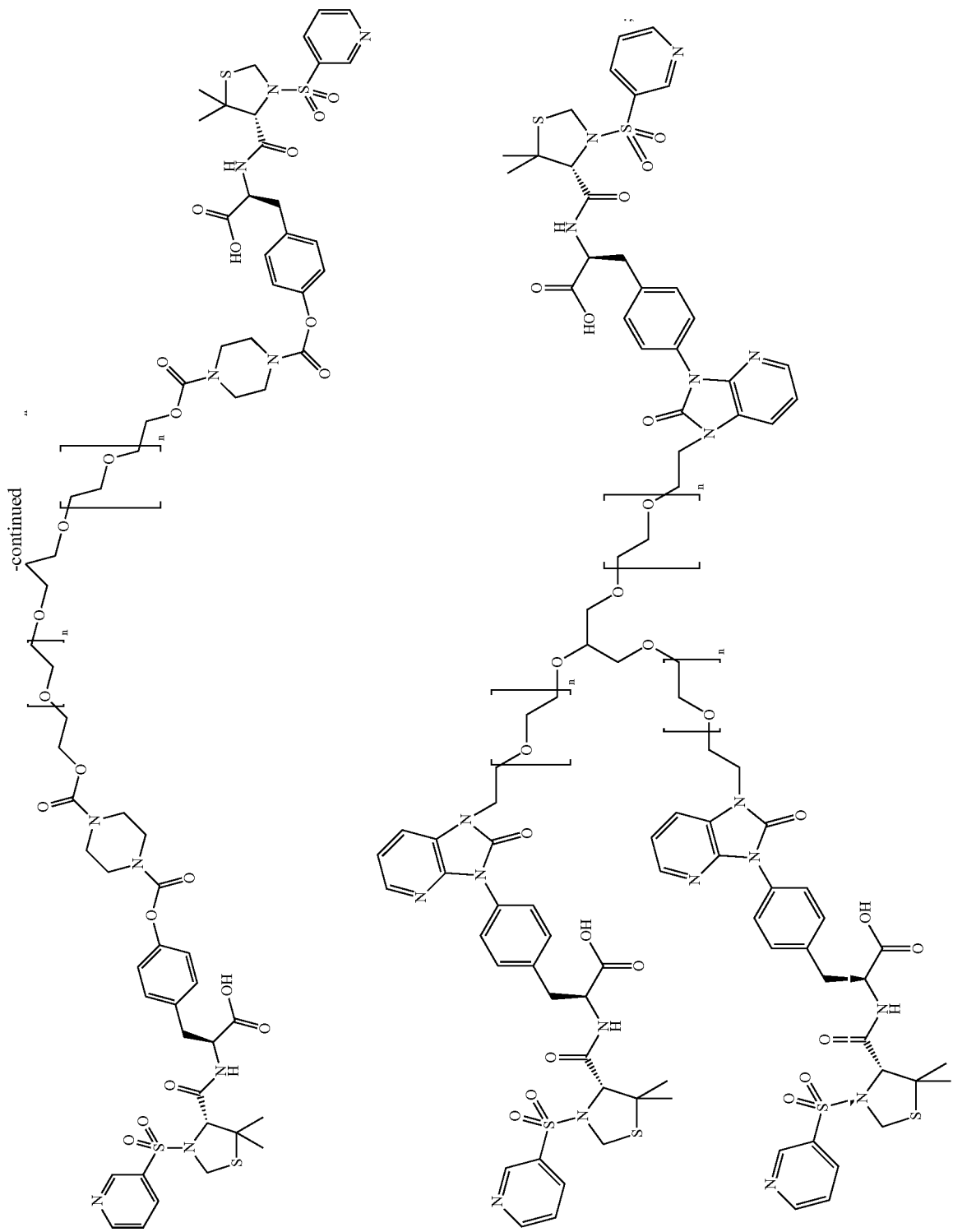

-continued
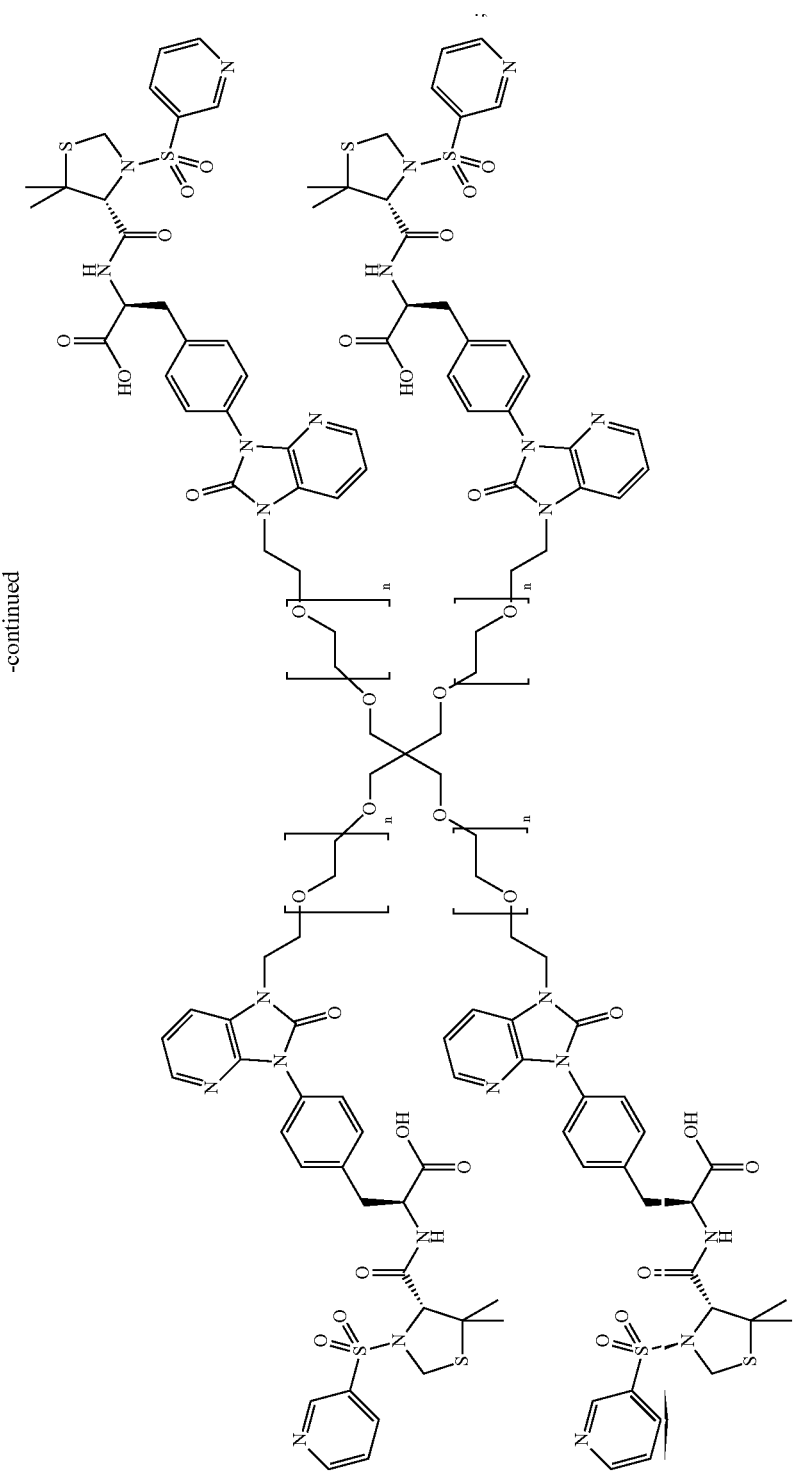

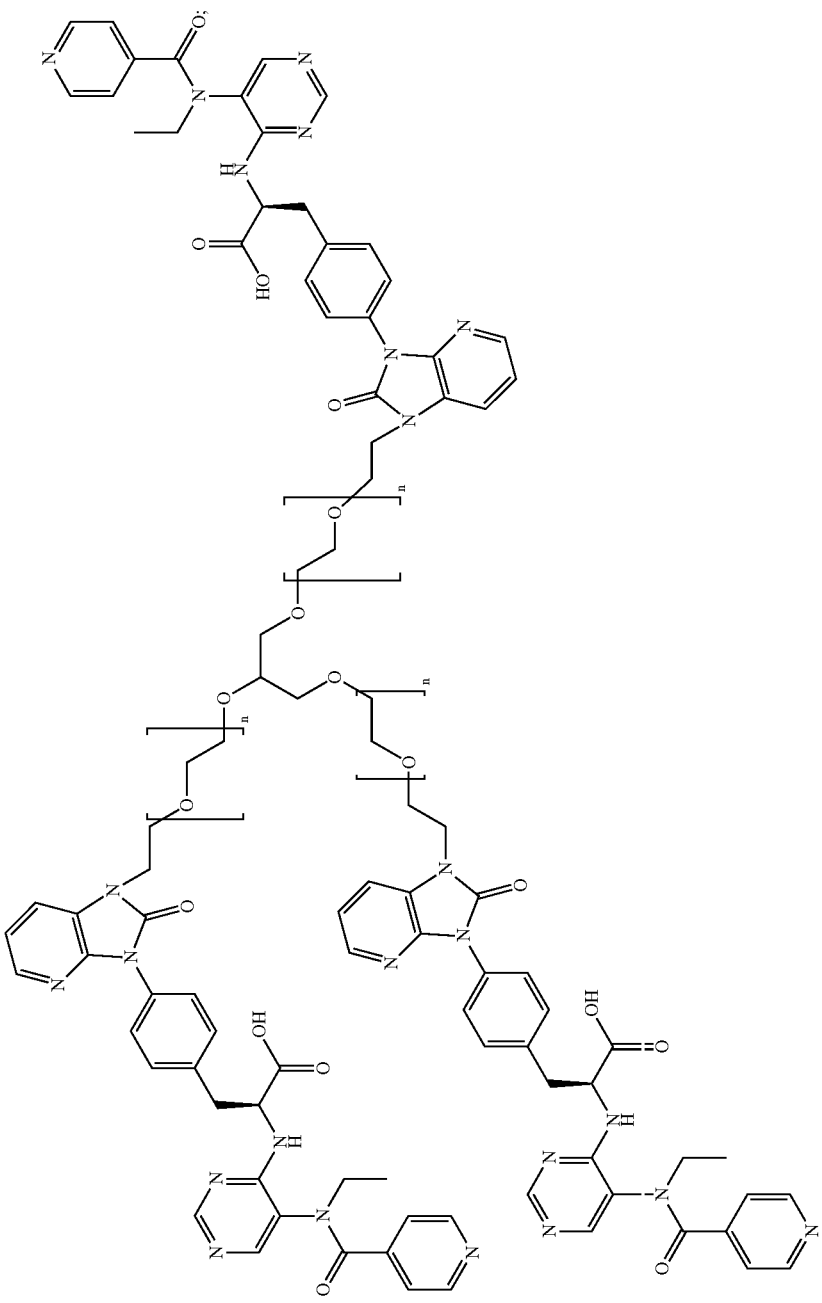

-continued
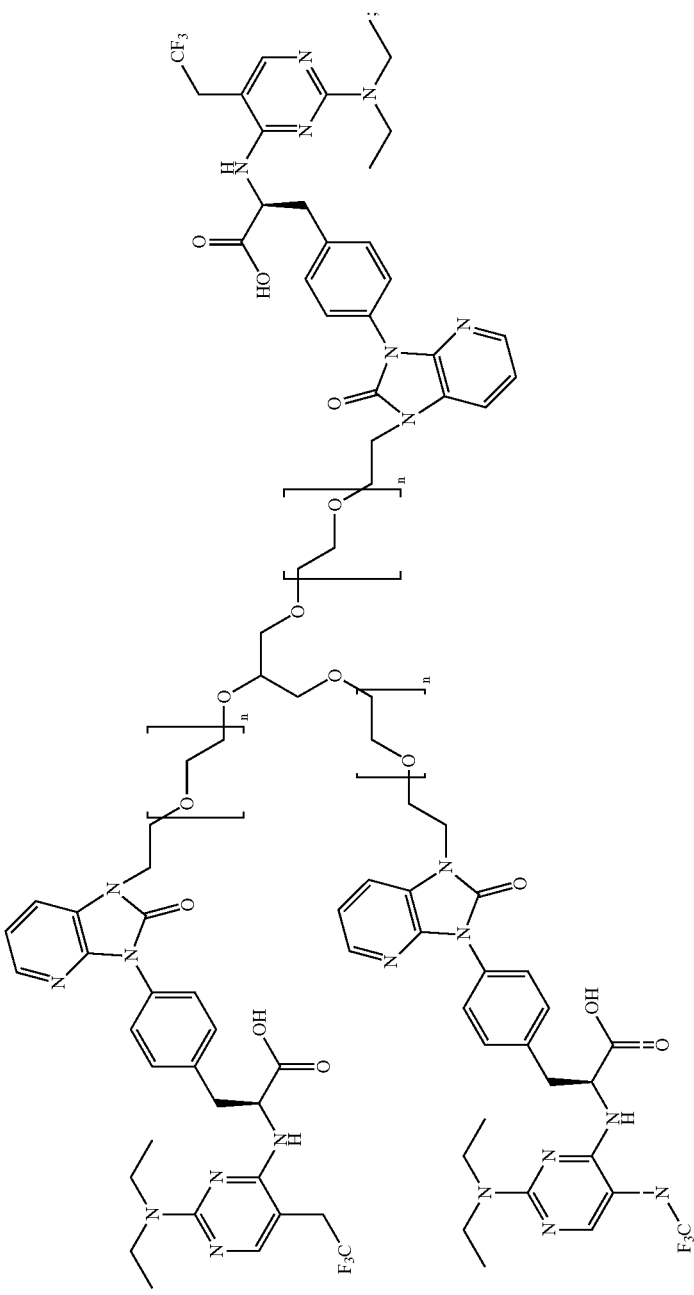

and pharmaceutically acceptable salts and ester thereof, and wherein the sum of all the variables "n" are sufficient to provide a total molecular weigh of the molecule between 20 kDa to 70 kDa, typically each n will be approximately the same, i.e. within 10-20%.

The amount of the alpha-4 inhibitory compounds In Groups I-VI required to achieve a therapeutic effect will vary with the particular compound, the route of administration, the age, sex, weight, and condition of the subject to be treated, and the particular disorder or disease to be treated.

For example, a suitable daily dose of the compound [1], and pharmaceutically acceptable salts thereof, for a mammalian subject suffering from, or likely to suffer from, any condition as described herein ranges from 0.1 to 100 mg per kilogram body weight of the mammalian subject, such as from 0.3 to 30 mg/kg of mammal body weight. In the case of parenteral administration, the dose may range from 0.1 to 10 mg of the compound per kilogram body weight, such as from 0.3 to 3 mg/kg of mammal body weight. In the case of oral dosing, a suitable daily dose may range from 1 to 100 mg of the compound per kilogram body weight, and further for example, may range from 2 to 30 mg of the compound per kilogram, and may be in the form of multiple daily dosages being 1 to 10 mg/kg of mammal body weight administered two to three times per day.

In the case of compounds of Group VII, exemplary modes of administration are subcutaneous injection or parenteral administration, e.g., by infusion. The therapeutic dosage of the conjugates of the present invention will vary according to, for example, the particular use for which the treatment is made, the manner of administration of the conjugate, the structure and molecular weight of the selected compound, the health and condition of the patient, and the judgment of the prescribing physician. For example, for subcutaneous administration, the dose will typically range from about 1-100 mg for a human patient administered between one time per week to one time per month, such as from about 5-75 mg about one time per week to about one time per month. Effective doses may be extrapolated from pharmacokinetic data such as maximum and minimum plasma concentrations over time derived from human dosing studies.

Relationship of Alpha-4 Inhibitory Compounds to Natalizumab

Natalizumab is a humanized IgG$_4$κ monoclonal antibody directed against the α-4-subunit of the heterodimeric alpha-4 integrins, α4β1 and α4β7. Natalizumab, like the disclosed alpha-4 inhibitory compounds, also binds alpha-4 integrins. It has already been shown that small molecules can specifically inhibit α$_4$ integrins, but clinical data are not yet available (N Engl J. Med. 348; 1 p. 68-72 January 2003). However, several clinical trials are underway with small molecules for the treatment of alpha-4-mediated diseases with compounds encompassed by or similar to compounds of the present invention. See, e.g., Pharmacokinetics, Safety, and Tolerability of R411, a Dual alpha-4-beta1-alpha-4-beta7 Integrin Antagonist After Oral Administration at Single and Multiple Once-Daily Ascending Doses in Healthy Volunteers. *J Clin Pharmacol* 44: 1368-1378 (2004)).

Thus, natalizumab and alpha-4 inhibitory compounds have the same or a very similar mechanism of action—causing inhibition of the α4-integrins binding to their several receptors as discussed above. Because the mechanisms are the same, the occurrence of PML may be a class wide serious adverse effect in alpha-4 inhibitory therapies.

Studies by Yednock and others have shown the clinical efficacy of α4-integrin blockade in experimental allergic encephalomyelitis (EAE), an animal model of MS (Yednock et al., *Nature* 1992; 356:63-66 (1992); Baron et al., *J. Exp. Med.* 177:57-68 (1993); Kent et al., *J. Neuroimmunol.* 58:1-10 (1995); Brocke et al., *Proc. Natl. Acad. Sci.* 96:6896-6901 (1999). These data demonstrated that α4-integrin blockade by a bound antibody can prevent leukocyte migration into the brain and thus support the hypothesis that α4-integrins are a target for MS therapeutics. In addition, these observations support the hypothesis that blockading leukocyte accumulation in the brain will prevent the local destruction of myelin, the insulating sheath covering nerve fibers, and neurons, which characterizes MS lesions. Natalizumab is the first antibody directed at this target and clinical data demonstrate the relevance of this treatment strategy.

Natalizumab is a member of an emerging class of agents known as the Selective Adhesion Molecule (SAM) Inhibitors. Natalizumab binding to α4β1 (also called VLA-4) and α4β7 integrins inhibits their molecular interactions with cognate integrin receptors on endothelial cells, VCAM-1 and MAd-CAM-1, respectively. By inhibiting these molecular interactions, natalizumab prevents the recruitment and egress of leukocytes into sites of inflammation. Alpha-4 inhibitor compounds have also demonstrated the same or similar modes of action in vivo models of alpha-4 mediated disease states (see, e.g., U.S. Published Application Nos. 20040138243 and 20040142954) and are expected to demonstrate the same or similar therapeutic properties as alpha-4 biologics. A further mechanism of natalizumab action may be to suppress ongoing inflammatory reactions in diseased tissues by inhibiting the interaction of α4-expressing leukocytes with other ligands in the extracellular matrix (osteopontin and fibronectin) and on parenchymal cells, such as microglial cells (VCAM-1). As such, natalizumab may suppress ongoing inflammatory activity at the disease site and inhibit further recruitment of immune cells into inflamed tissues. Thus, treating MS patients with natalizumab may block entry of mononuclear leukocytes into the CNS and attenuate the inflammatory process that results in demyelination and axonal damage and ultimately provide clinical benefit by reducing the number of clinical relapses and the progression of disability, including motor, visual, and cognitive function. In addition to treatment of MS, alpha-4 inhibitors have been shown to have activity in other disease states. Natalizumab is presently under consideration for approval for Crohn's Disease, and underwent clinical trials for rheumatoid arthritis. Multiple studies have also demonstrated that alpha-4 integrin antagonists have activity in treatment of experimental models of asthma. See for example, "A small-molecule, tight-binding inhibitor of the integrin alpha-4-beta1 blocks antigen-induced airway responses and inflammation in experimental asthma in sheep" in *American Journal of Respiratory & Critical Care Medicine.* 162(2 Part 1). August, 2000. 603-611.

Safety of Natalizumab

The safety profile of natalizumab is demonstrated herein, and based on results of treating 3,919 subjects with natalizumab in clinical trials for MS, Crohn's Disease, and rheumatoid arthritis, resulting in 5,505 patient-years of natalizumab exposure. Treatment with natalizumab was generally well tolerated. Eighteen treatment-emergent deaths occurred in the entire natalizumab program. The adverse events encountered in the trials, both common and serious, were similar in natalizumab-treated patients and controls. Adverse events that led to discontinuation of natalizumab occurred in 5.8% of natalizumab-treated MS patients and in 4.8% of placebo-treated MS patients, with urticaria being the most common cause of discontinuation in the natalizumab-treated patients (1.2%).

Like other highly active drugs used to treat autoimmune diseases, natalizumab is not without risk. Unfortunately, with the clinical efficacy of immunomodulatory agents such as natalizumab and other alpha-4 inhibitor compounds comes the risk of significant mechanism-based side effects. The risks of medications that modulate immune function in order to treat serious chronic diseases have been well recognized over the past several years. Medicines such as the TNFα antagonists (e.g., infliximab, adalimumab, and etanercept) are potent modulators of immune function and are approved for numerous serious autoimmune diseases such as rheumatoid arthritis, Crohn's Disease, psoriasis, psoriatic arthritis, and ankylosing spondylitis. Although very effective in some cases, these agents are associated with serious adverse events, particularly infections that have been associated with significant morbidity and mortality.

The invention provides the identification, through detailed safety analyses, of PML as a rare, but significant, risk of treatment with alpha-4 inhibitors. In addition, serious non-PML opportunistic infections have been observed in natalizumab-treated patients, mostly in Crohn's Disease patients in association with concurrent immunosuppressant use or other significant co-morbidities. In addition, patient populations were identified in whom the benefit-risk profile is less well defined. The occurrence of these infections highlights the need for a comprehensive risk management program in the post-marketing setting focused on appropriate use conditions and assessment and minimization of the risk of PML and other serious opportunistic infections.

Deaths

Of the eighteen deaths that occurred during the clinical trials, five occurred in the placebo-controlled MS trials (including two in patients who had received natalizumab and three who had received placebo). The patients who received natalizumab died of alcohol intoxication and metastatic malignant melanoma. The patients who received placebo died of cardiac arrest, respiratory arrest, and pleural carcinomatosis with seizures. Four deaths occurred in the open-label MS trials, due to respiratory distress, PML, suicide, and seizure due to MS.

Six deaths of natalizumab-treated Crohn's Disease patients were observed in the trials. The exposure to natalizumab was approximately three-fold greater in these trials than exposure to placebo. The causes of death were acute myocardial infarction, acute renal failure, carbon dioxide asphyxiation, PML, *pneumocystis carinii* pneumonia, and bronchopulmonary aspergillosis.

Three deaths occurred in the rheumatoid arthritis trials, two in natalizumab-treated patients and one in a patient treated with a placebo. The natalizumab-treated patients died of hemoptysis with respiratory failure and end-stage rheumatoid pulmonary disease. The placebo-treated patient died of circulatory and respiratory insufficiency.

In the MS studies, apart from PML, no other safety signal was apparent from the study deaths. In the Crohn's Disease studies, one patient died from PML. Two additional deaths in Crohn's Disease were associated with opportunistic infections, namely, bronchopulmonary aspergillosis and *pneu-*

*mocystis carinii* pneumonia. These patients had significant co-morbidities, which may have contributed to the development of these infections.

Adverse Events

At least one serious adverse event was encountered by 251 of the 1,617 natalizumab-treated MS patients (15.5%) and by 214 of the 1,135 placebo-treated patients (18.9%) in the placebo-controlled trial. The most common serious adverse events, classified by organ systems, were nervous system disorders (5.9% natalizumab, 10.2% placebo). MS relapse contributed significantly to this incidence (4.7% natalizumab, 9.0% placebo). The second most common serious adverse events were infections and infestations (2.4% natalizumab, 2.2% placebo), with appendicitis and urinary tract infection (<1% in both groups) as the most common.

The incidence of hypersensitivity reactions, an event expected to result from treatment with therapeutic proteins, was approximately 4% with serious systemic reactions occurring at an incidence of less than 1%. The reactions tended to occur early in the treatment course, but were observed throughout the course of infusion. Although the specific mechanisms of the reactions have not been determined, clinically, the reactions appeared to be typical IgE- or IgG-mediated immediate-type hypersensitivity reactions. All patients recovered without sequelae.

The occurrence of malignancy during natalizumab treatment was uncommon. The incidence of malignancy was balanced between the natalizumab and control groups. The rates of malignancies observed during natalizumab treatment were within the expected rates per comparison with the existing cancer registries, such as the National Cancer Institute's Surveillance Epidemiology and End Results.

Evaluation of PML Cases

Three confirmed cases of PML have been identified, two of which were fatal. Two cases occurred in MS patients and one in a patient with Crohn's Disease. Both MS patients received natalizumab for over two years in addition to AVONEX®. The Crohn's Disease patient received eight doses of natalizumab over an 18-month period and was immunocompromised due to chronic azathioprine use as manifested by persistent lymphopenia. All three PML patients presented with subtle clinical changes early in their disease course that were noted by the patients or their families.

The first patient to contract a fatal case of PML was a 46-year-old female with MS who presented to her neurologist with right-sided paresthesia and dysesthesia, and right upper extremity clumsiness. MRI brain scanning demonstrated four non-enhancing T2-hyperintense lesions bilaterally in the corona radiata. Six weeks later, she presented with new blurring of the vision in her right eye. Visual acuity was 20/15 in the left eye and 20/100 in the right. Spinal fluid analysis yielded one white blood cell, normal protein and glucose, and no oligoclonal bands. A follow-up MRI brain scan revealed two new subcortical lesions in the right parietal region that were hyperintense on FLAIR imaging and hypointense on T1.

AVONEX® treatment was initiated, but she subsequently suffered three relapses, the most recent of which involved band-like pain around the abdomen, lower extremity weakness, and spasticity requiring treatment with methylprednisolone. Her Expanded Disability Status Scale (EDSS) score in prior to entry into the placebo-controlled MS study, as described in more detail below, was 2.5. She received 30 infusions of natalizumab before entering the open-label extension study and receiving an additional seven infusions. She had no exacerbations or suspected relapses during her time in the placebo-controlled study. She developed five new or enlarging T2-hyperintense lesions during the first year of the placebo-controlled study and one during the second year. She was negative for anti-natalizumab antibodies and her serum concentration of natalizumab was similar to the mean of the study populations throughout her participation.

In November 2004, she began to experience motor dysfunction, and cognitive and language difficulties, which progressed to right hemiparesis by the following month. An MRI brain scan performed in December 2004 revealed left frontal T2-hyperintensity and T1-hypointensity with extension into the centrum semiovale and corona radiata without Gd-enhancement. She received two courses of high dose steroids over the next few months, but continued to decline. She received her last dose of natalizumab on Jan. 18, 2005. She was readmitted to the hospital on Feb. 12, 2005, with worsening clinical status. A repeat MRI brain scan in February 2005, showed extension of the lesion seen previously. An extensive work-up over the next week revealed JC viral DNA in the CSF, resulting in the diagnosis of PML. She died on Feb. 24, 2005. Post-mortem examination revealed normal organs without evidence of opportunistic infection. The brain examination revealed extensive, severe cavitation mainly in the left hemisphere as well as multiple non-cavitated, ovoid areas throughout the white matter of both hemispheres typical of PML, having reactive astrocytes with enlarged, hyperchromatic nuclei (Kleinschmidt-DeMasters and Tyler, *N. Engl. J. Med.* 353:369-374 (2005)).

The second patient was a 46-year-old male who experienced his first symptoms of relapsing/remitting MS in 1983. His past medical history is significant for auricular zoster, Ramsay-Hunt syndrome, and melanoma. His family history is notable for a sister with MS. He had been treated with AVONEX® since 1998, and experienced three relapses the year before enrolling in the placebo-controlled MS study, during which he experienced no relapses or evidence of progression. He was negative for anti-natalizumab antibodies and his serum concentration of natalizumab was similar to the mean of the study populations throughout his participation.

In October 2004, his MRI scan showed a small periventricular Gd-enhancing lesion on the right and a small right frontal, subcortical, non-enhancing, T2-hyperintense lesion. In November 2004, he exhibited behavioral changes followed by hemiparesis and cognitive impairment. H is last dose of natalizumab was in December 2004. In February 2005, despite treatment with high dose intravenous methylprednisolone, he continued to deteriorate. A brain MRI scan in February 2005, demonstrated extension of the previously identified lesion. He underwent an extensive work-up, including CSF analysis and brain biopsy, which resulted in the diagnosis of PML. Cidofovir treatment was initiated without clinical effect. The JC viral load decreased in his plasma and CSF over the next few months. This corresponded to further deterioration in his clinical course and development of Gd-enhancing lesions on MRI, consistent with Immune Reconstitution Inflammatory Syndrome. He continued to receive treatment with cidofovir, and cytarabine was added. Approximately 3 months following discontinuation of natalizumab, he began to improve. He is able to converse and can hold high-level conversations about his medical course and treatment, but has significant residual cognitive impairment with left hemiparesis and ataxia (Langer-Gould et al., *N. Eng. J. Med.* 353:375-381 (2005)).

The final patient was a 60-year-old male with a 28-year history of Crohn's Disease. Over the course of his illness, he had been treated with azathioprine, oral budesonide, corticosteroids, and four doses of infliximab. He displayed pre-existing signs of impaired hematopoiesis, predominantly lymphopenia and anemia, since 1996 and received azathioprine beginning in 1999. He was enrolled in a Phase 3 study of natalizumab in patients with active Crohn's Disease in March 2002, and received three doses concomitantly with azathioprine prior to being randomized to placebo in a Phase 3 maintenance study. He remained on azathioprine and placebo until November 2002, when azathioprine was discontinued due to refractory pancytopenia. In February 2003, he began open-label treatment with natalizumab. He was negative for anti-natalizumab antibodies and his serum concentration of natalizumab was similar to the mean of the study populations throughout his participation.

In July 2003, one month after his fifth dose of natalizumab, he presented with a one-week history of cognitive decline. A brain MRI scan demonstrated a large T2-hyperintense lesion in the right frontal lobe, and additional hyperintense lesions in the left frontal and temporal lobes that did not enhance with gadolinium. He underwent a partial resection of the lesion, the pathology of which was read at the time as an anaplastic astrocytoma, WHO Grade III. He was treated with corticosteroids and anticonvulsants, but was too ill for radiation therapy. Follow-up MRI six weeks after surgery showed tumor extension. He deteriorated clinically and died in December 2003. The case was reported by the treating physician as a malignant astrocytoma, based upon the final pathology report. In February, as a result of the one confirmed and one suspected case of PML described above, his case was reassessed and determined to be PML following consultation with two independent neuropathologists with expertise in PML (Van Assche et al., *N. Engl. J. Med.* 353:362-368 (2005)).

Clinical trial patients exposed to natalizumab were systematically assessed for evidence of incipient PML or any other opportunistic infection. Patients were evaluated if they had any active neurological deterioration for which PML could not be excluded as a diagnosis, showed MRI abnormalities for which PML could not be ruled out, or their CSF had detectable JCV DNA titers.

Criteria were established prospectively for the neuroradiologic evidence and laboratory assays for the diagnosis of PML. A diagnosis of "confirmed PML" was defined by presence of progressive clinical disease, MRI signs typical of PML, detection of JCV DNA in CSF, or pathologic confirmation. Sufficient evidence to exclude PML was defined as lack of progressive neurological disease, MRI lesions not typical of PML or stable over time, or no detectable JCV DNA in the CSF if the MRI was suspicious. A case was deemed "indeterminate" if there was clinical or MRI suspicion of PML and follow-up clinical, MRI, or CSF data could not be obtained.

A total of 3,826 eligible study participants (2,248 MS patients, and 1,578 Crohn's Disease/rheumatoid arthritis patients) were notified to report to their treating physician/investigators for an assessment. Investigators were requested to perform the assessment procedure, including medical history, neurological examination, brain MRI, and CSF collection. Blood samples were also collected for PCR analysis of JCV DNA as an exploratory adjunct. MRI scans were assessed by Central Reader Centers with expertise in neurological disorders, including the two Central Reader Centers for the original Phase 3 MS studies. A consensus guideline was developed prospectively to standardize criteria to help distinguish MS white matter abnormalities from those of PML.

In all, 3,389 (89%) study patients with MS, Crohn's Disease, or rheumatoid arthritis were assessed by their treating physician, 3,116 of whom had received natalizumab. The remaining 273 patients had received placebo as part of a clinical trial and were included as a control group. Of the 437 that were not assessed, 60 (22 MS patients, 38 Crohn's Disease/rheumatoid arthritis patients) were lost to follow-up. Amongst the 3,389 patients who participated, 2,046 were MS study patients, over 97% of whom were seen within three months of their last natalizumab dose. Six MS patients were referred for further evaluation. Of these clinical trial patients, five were referred due to neurological worsening and one due to possible PML based on MRI findings. MRI scan review effectively ruled out the diagnosis of PML in the five patients referred based on clinical concern. Repeat MRI and CSF analysis excluded PML in the case referred based on MRI findings.

Of the 1,349 Crohn's Disease/rheumatoid arthritis patients who participated in the safety evaluation, 21% were seen within three months of their last dose, 91% within six months. Thirty-five patients were evaluated, including one due to clinical or neurological symptoms, 32 based on suspicious changes on MRI, one due to high plasma JCV copy number, and one due to an inability to perform MRI in a patient with a normal neurological examination. The higher rate of examination of Crohn's Disease compared to MS was predominantly driven by the lack of baseline MRI scans for comparison in the Crohn's Disease population. Most cases were deemed not to be PML based on review of neurological examination, MRI and, if available, CSF testing. For the ten cases in which concern still remained, repeat MRI assessments were performed and all were diagnosed as "not PML" based on lack of clinical progression, lack of MRI progression over two months following the initial MRI leading to referral for evaluation, and in some cases, results of CSF testing.

MRI scans of the brain with and without Gd-enhancement and a FLAIR sequence were sometimes a useful tool for excluding a diagnosis of PML in the MS cases. The existence of pre-treatment and on-treatment MRI scans increased specificity and assisted in interpretation of the follow-up MRI scans obtained at varying time points, especially in the setting when the patient's neurological condition was worsening. During the safety evaluation process, comparison to previous scan was required in approximately 35% percent of MS cases because of the presence of lesions for which PML could not be definitely excluded. After comparison to a prior scan, the neuroradiologist was able to exclude PML in greater than 99% of MS cases.

CSF was available for testing in 396 patients who had been treated for MS or Crohn's Disease with natalizumab. JCV was not detected in any of these cases, including 19 patients evaluated based on clinical or MRI criteria. Samples from 411 patients with MS and other neurological disorders served as CSF and plasma controls and were evaluated in collaboration with the Karolinska Institute and the National Institutes of Health (Yousry et al., *N. Engl. J. Med.* scheduled for publication Mar. 2, 2006). No detectable JCV was found in these CSF samples, confirming the specificity of the CSF assay for only active cases of PML. Each of the three patients with confirmed PML had detectable JCV DNA. A previous study had indicated that JCV was found in 11% of the biological specimens of the 121 MS patients tested (Ferrante et al., *Multiple Sclerosis* 4:49-54 (1998).

Plasma was tested for the presence of JCV DNA as an exploratory measure. The entire consenting study population (2,370 patients) was evaluated using a high-throughput automated system of DNA extraction and PCR analysis. In addition, a random subset of samples was assessed using a manual low-throughput method. Although the manual method was demonstrated to be an order of magnitude more sensitive than the high-throughput system, given the techniques involved, testing using this method was only possible in approximately 10% of the overall population (209 patients). Of the 2,370 patients from the safety evaluation who were tested for JC viremia, only five patients (0.2%) had detectable JCV DNA, three of whom had never received natalizumab. In addition, JCV DNA was not detected in any of the 411 samples from MS patients naïve to treatment and patients with other neurological diseases. These results were confirmed using the manual extraction method. In addition, of the random subset of 209 patients tested by the manual method, an additional five (2.4%) samples had detectable JCV DNA. None of the patients with detectable JCV DNA in their plasma by either method had clinical features or MRI findings suggestive of PML.

Serum samples were available from the three patients with confirmed PML obtained both before and after diagnosis. Only one patient, the patient with Crohn's Disease, had detectable JCV DNA in the serum prior to the onset of his symptoms. The other two patients had no detectable JCV DNA despite being clinically symptomatic for the disease and manifesting changes on a brain MRI scan. The observations in these groups of patients are consistent with the data from the literature demonstrating that the mere presence of JCV DNA in plasma is neither predictive nor diagnostic of PML.

In summary, the comprehensive safety assessment performed following the identification of PML in natalizumab-treated patients uncovered no additional confirmed cases of PML in the over 3,000 patients examined. Nearly all patients who had received natalizumab in recent MS, Crohn's Disease, and rheumatoid arthritis studies were accounted for during the assessments, making it unlikely that any cases of PML were missed. The occurrence of PML was limited to two MS cases and one Crohn's Disease case, as originally described. The incidence of PML in subjects treated with natalizumab in MS and Crohn's Disease clinical trials is therefore approximately 1/1,000 with a 95% confidence interval ranging from 0.2 to 2.8/1,000. Plasma testing proved to be neither predictive nor diagnostic of PML, consistent with the published literature (Kitamura et al., *J. Infect. Dis.* 161:1128-1133 (1990); Tornatore et al., *Ann. Neurol.* 31:454-462 (1992); Dorries et al., *Virology* 198:59-70 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9 (Suppl 1):81-87 (2003)). Clinical and MRI abnormalities were present in two of the three patients with PML before JCV DNA was detected in the plasma. In addition, JCV DNA was detected in plasma in several subjects in the study who had no clinical or radiographic signs of PML, including three who had never received natalizumab. These results suggest that establishing one static level of plasma JCV is not useful in predicting the likelihood of PML in asymptomatic patients. Physicians and patients should remain vigilant for signs and symptoms of PML and have a low threshold to suspend treatment and initiate appropriate diagnostic work-up (MRI, CSF analysis) in natalizumab-treated patients presenting with new neurological decline.

Drug Interactions

In a placebo-controlled MS study, the administration of AVONEX® appeared to be associated with an increase in the serum concentrations of natalizumab in a small cohort on whom intensive pharmacokinetic sampling was performed. However, based upon a comparison of the mean post-hoc parameter estimates from the population pharmacokinetic analysis, steady-state clearance and half-life values differed between patients concurrently taking AVONEX® and natalizumab monotherapy, but only by approximately 5%, and were not considered clinically significant. In addition, natalizumab was well tolerated when administered to 589 patients in combination with AVONEX® for up to 120 weeks. It is notable that the two reports of PML in the MS database occurred in patients receiving concomitant AVONEX®. Thus, the risk of PML with natalizumab treatment may be increased by concomitant treatment with interferon β, though this could have occurred in two patients on combination therapy due to chance alone (p=0.23).

The safety of natalizumab in combination with glatiramer acetate was evaluated by administering natalizumab over six months to patients who continued to receive 20 mg of daily glatiramer acetate. There were no interactions between glatiramer acetate and natalizumab pharmacokinetics or its α4-integrin receptor saturation. However, this study was of insufficient size or duration to establish the long-term safety or efficacy in this population.

Efficacy of Natalizumab

Multiple Sclerosis

MS is a chronic disease of the brain and spinal cord. In temperate zones such as the United States, the incidence of MS is approximately 1 to 5/100,000 per year (US National MS Society; NMSS), with a US prevalence estimated at 350,000 to 400,000. It is a disease of young adults, primarily women, with disease onset typically occurring between the ages of 20 and 40. The first clinical manifestations of MS usually take the form of a clinically isolated syndrome affecting the optic nerve (optic neuritis), spinal cord (transverse myelitis), or brainstem/cerebellum (Runmarker and Anderson, *Brain* 116:117-134 (1993)). Estimates of the number of patients who eventually go on to develop MS vary widely, but, in the case of optic neuritis, the presence of MS-like lesions on MRI at the time of the attack indicates a greater than 80% chance of developing clinically definite MS within 10 years (O'Riordan et al., *Brain* 121:495-503 (1998); Sailer et al., *Neurology* 52:599-606 (1999)).

Demyelination and nerve fiber transection is thought to occur when activated T lymphocytes cross the blood-brain barrier and initiate a series of events leading to activation of endothelial cells, recruitment of additional lymphocytes and monocytes, and release of pro-inflammatory cytokines. MS lesions typically consist of immune cells, demyelinated axons, oligodendrocytes attempting remyelination, proliferating astrocytes, and varying degrees of axonal transection. Cytokines such as tumor necrosis factor-alpha (TNF-α) and interferon gamma (IFN-γ) interact with immune cells, amplifying this process. The initiating event of the inflammatory cascade is unknown; however, adhesion and trans-endothelial migration of inflammatory cells from the bloodstream across the blood-brain barrier and into the central nervous system (CNS) is thought to be an early and critical step in this process.

Emerging data demonstrate that irreversible axonal loss occurs early in the course of MS. Because transected axons fail to regenerate in the CNS, early effective treatment aimed at suppressing MS lesion formation is of paramount importance. As early as disease onset, axons are transected in lesions with active inflammation (Trapp et al., *N. Engl. J. Med.* 338:278-285 (1998); Bjartmar and Trapp, *Curr. Opin. Neurol.* 14:271-278 (2001); Ferguson et al., *Brain* 120 (Pt 3):393-399 (1997)). The degree of demyelination is related to the degree of inflammation and the exposure of demyelinated axons to the inflammatory environment, as well as non-inflammatory mediators (Trapp et al., *N. Engl. J. Med.;* 338: 278-285 (1998); Kornek et al., *Am. J. Pathol.* 157:267-276 (2000); Bitsch et al., *Brain* 123:1174-1183 (2000)). There is also destruction of oligodendrocytes with impaired remyelination in demyelinating lesions (Peterson et al., *J. Neuropathy Exp. Neurol.* 61:539-546 (2002); Chang et al., *J. Neurovirol.* 8:447-451 (2002)). The loss of oligodendrocytes leads to a reduction in the capacity to remyelinate and may result in the loss of trophic factors that support neurons and axons (Bjartmar et al., *J. Neurocytol.* 28:383-395 (1999)).

The typical inflammatory lesions of MS can occur throughout the CNS, but certain sites seem particularly vulnerable, such as the optic nerve, brainstem, spinal cord, and periventricular regions of the cerebrum. It is the resulting loss of myelin and nerve fibers in these areas that leads to impaired neuronal conduction and symptoms such as weakness, sensory loss, visual loss, double vision, and imbalance. In relapsing remitting MS, these episodes of demyelination typically result in several weeks of neurological dysfunction followed by partial or full recovery. However, more severe attacks may result in permanent deficits. The recurrent attacks over time lead to accumulating physical disability and cognitive decline.

A number of measures, including clinical measures, those based on MRI scans, and those based on quality of life, can be used to assess a product's efficacy in treating MS. The Expanded Disability Status Scale (EDSS) is an extensively used tool for tracking the course of disability in MS. It classifies the most common MS-associated neurological impairments into disability levels ranging from 0 to 10, with each successive step describing a worsening of disease. In the lower range of the EDSS scale, disease progression is primarily defined by increasing levels of disability in specific functional systems measured during neurological examination. Scores of 1.0 through 3.5 describe mild to moderate disability in the functional systems. Higher scores, in the range of 4.0 and above indicate increasingly severe disability that affects ambulation, including the need for assistive devices such as a cane (an EDSS of 6.0), a walker (an EDSS of 6.5), or a wheelchair (an EDSS of 7.0). Scores higher than 7.0 classify patients confined to bed.

The MS Functional Composite (MSFC) (Whitaker et al., *Multiple Sclerosis* 1:37-47 (1995)) is also used to assess efficacy. Unlike traditional MS clinical outcome measures that are derived from the standard neurological examination, the MSFC is based on quantitative tests of leg function/ambulation (the Timed 25-Foot Walk), arm function (the Nine-Hole Peg Test), and cognitive function (the Paced Auditory Serial Addition Test (PASAT 3)) which expand upon the measurements of the EDSS and assess effects in clinical dimensions not well captured by this scale.

MRI is another tool for assessing efficacy in treating MS and can be used alone or to support clinical data to assess therapeutic effects on relapse and disability endpoints. MRI is a sensitive tool for monitoring disease activity, detecting approximately five to ten times more disease activity in both relapsing remitting MS and secondary progressive MS patients than is clinically apparent (Isaac et al., *Neurology* 38:1511-1515 (1988); Willoughby et al., *Ann. Neurol.* 25:43-44 (1989); Khoury et al., *Neurology* 44:2120-2124 (1994); Thompson et al., *Ann. Neurol.* 9:53-62 (1991); Thompson et al., *Neurology* 42:60-63 (1992)). T2-weighted sequences in MS patients detect new areas of acute demyelination, as well as more chronic areas of demyelination and gliosis. For this reason, T2-weighted MRI is a good technique for monitoring the accumulation of lesions over time, either as a count of active lesions or a change in the total volume of such lesions.

Infusion of gadolinium-diethylenetriamine pentaacetic acid (Gd-DPTA) during acquisition of T1-weighted sequences allows for visualization of blood-brain barrier breakdown secondary to the inflammation characteristic of acute MS lesions. The evidence to date suggests that gadolinium (Gd)-enhancement is a useful marker of disease activity that correlates with clinical relapse (Molyneux et al., *Ann. Neurol.* 43:332-339 (1998); Kappos et al., *Lancet* 353:964-969 (1999); McFarland et al., *Multiple Sclerosis* 8:40-51 (2002)).

New hypointense lesions on T1-weighted sequences in MS patients correspond either with inflammatory Gd-enhancing lesions (comprising edema, demyelination, axonal loss, or combinations of these pathologies) (Bruck et al., *Ann. Neurol.* 42:783-793 (1997)) or as chronic lesions with considerable axonal loss. Approximately half of the acute T1 hypointensities on MRI will evolve into chronic "T1 black holes," which correlate with disability progression (Simon et al., *Neurology* 55:185-192 (2000)).

As described in more detail in Example 1, two Phase 3 studies were conducted to study the effect of two years of treatment with natalizumab. One of the studies used natalizumab alone (the monotherapy study) and the other used natalizumab in combination with AVONEX® (the add-on therapy study). Both these Phase 3 studies were designed with two sets of primary and secondary endpoints. The primary and secondary endpoints were selected to measure the effects of natalizumab on the inflammatory aspects of the disease after a mean of one year of follow-up in each study (900 patient-years of observation in the monotherapy study; 1,200 patient-years in the add-on therapy study).

The primary endpoint of these studies was the annualized rate of clinical relapses. Two of the secondary endpoints were two supporting MRI measures of inflammatory disease activity, namely, the mean number of new or newly enlarging T2-hyperintense lesions (measuring lesion accumulation over time) and the mean number of Gd-enhancing lesions (measuring acute disease activity), as ranked in order of importance. The proportion of patients remaining relapse-free provided a third secondary endpoint.

Another series of endpoints was assessed at the conclusion of each study following two years of natalizumab treatment. The endpoints for this final analysis were selected to determine natalizumab's effects on measures associated with MS disease progression. The primary endpoint at two years was the time until onset of sustained progression of disability, as measured by changes in EDSS scores. Similar to the one-year analysis, the secondary endpoints were additional MRI and clinical measures that would support the primary analysis. The secondary endpoints at two years, ranked in order of importance, were the rate of MS relapses (to confirm one-year relapse observations), the mean volume of T2-hyperintense lesions (a measure of overall MS disease burden), the mean number of T1-hypointense lesions (a measure of axonal loss), and progression of disability as determined by changes in the MSFC (to confirm and expand upon disability effects as measured by the EDSS).

Given two primary endpoints at two different time points (annualized relapse rate at one year, time to disability progression at two years), the Hochberg procedure for multiple comparisons (Hochberg, *Biometrika* 75:800-802 (1988)) was used to evaluate the primary endpoint. Each set of secondary endpoints was prioritized in order of importance as listed above. A closed testing procedure was used for each set, such that if statistical significance was not achieved for an endpoint within a set, all endpoints(s) of a lower rank in that set were not considered statistically significant. Analyses of tertiary endpoints did not include adjustments for multiple comparisons.

Monotherapy with Natalizumab

These results of the monotherapy study indicated that natalizumab is an effective treatment as monotherapy for relapsing remitting MS. Natalizumab treatment resulted in significant effects on relapse rates, disability progression, and all MRI measures, the primary and secondary endpoints of the study. Analysis of Kaplan-Meier curves indicate that the impact on relapse rates and disability progression was apparent early after treatment initiation, and was sustained throughout the treatment period with patient groups continuing to diverge at the final timepoint. Further, these findings were consistent across subgroups. Additional positive effects were seen on measures of relapse severity and quality of life.

MS patients treated with natalizumab alone had a 42% lower risk of their disability progressing compared to placebo, as measured by changes on the EDSS, the primary endpoint of the study at two years ($p<0.001$). The percentage of patients estimated to progress was 17% and 29% with natalizumab and placebo, respectively. In addition to the EDSS, natalizumab had significant effects on all relapse endpoints studied over two years, including a 68% reduction in the annualized relapse rate compared to placebo, with 67% of natalizumab-treated patients remaining relapse-free, compared to 41% of patients on placebo. The MRI scans supported these clinically-observed effects. Also, natalizumab treatment improved the patients' quality of life, as measured by the physical and mental components of the SF-36. All these effects were consistent and significant across subgroups defined by baseline demographics and disease activity.

Combination Therapy of Natalizumab and AVONEX®

A significant number of patients who receive the currently approved therapies continue to experience disease activity, as measured both clinically and by MRI. This is an expected outcome of these partially effective approved medications, each of which leads to an approximately 30% reduction in relapse rate (IFNB MS Study Group, *Neurology* 43:655-661 (1993); Jacobs et al., *Ann. Neurol.* 39:285-289 (1996); PRISMS Study Group, *Lancet* 352:1498-1504 (1998); Johnson et al., *Neurology* 45:1268-1276 (1995)). Data from the Phase 3 trials of βinterferon for the treatment of MS show that 62% to 75% of patients experienced at least one relapse during these two-year trials despite interferon treatment IFNB MS Study Group, *Neurology* 43:655-661 (1993); Jacobs et al., *Ann. Neurol.* 39:285-289 (1996); PRISMS Study Group, *Lancet* 352:1498-1504 (1998)). Similarly, 66% of subjects in the Phase 3 MS trial of glatiramer acetate experienced at least one relapse during the 2-year period, a number that was not significantly different from placebo (Johnson et al., *Neurology* 45:1268-1276 (1995)). Although a variety of therapeutic strategies are currently in use in clinical practice to manage breakthrough disease while on treatment (e.g., switching therapy, changing dose and frequency of interferon, combination therapy), these practices are largely empirical as there are no randomized, controlled trials to assess the efficacy of these approaches.

The add-on therapy study was designed to evaluate the efficacy of natalizumab against active control for patients breaking through AVONEX® monotherapy. The choice of β-interferon was supported by available data on the proposed mechanisms of action of the available drugs. As discussed above, natalizumab has a well-defined mechanism of action, specifically targeting cellular adhesion and trans-endothelial migration via α4-integrins, as do the class of alpha-4 inhibitor compounds. Although the exact mechanism by which interferon-β exerts efficacy in MS is not known, interferon-β induces a large number of cellular processes involved in cytokine secretion and cellular phenotype changes. Interferon-β down regulates interferon-γ induced MHC class II molecule production, decreases secretion of TH1 pro-inflammatory cytokines (TNF-α, IL-2 and interferon-γ) and increases secretion of TH2 anti-inflammatory cytokines (IL-4 and IL-10) (Rep et al., *J. Neuroimmunol.* 67:111-118 (1996); Kozovska et al., *Neurology* 53:1692-1697 (1999); Rudick et al., *Neurology* 50:1266-1272 (1998)). In addition, interferon-β may affect leukocyte trafficking through suppression of the chemokines RANTES and MIP-1α, as well as their receptor CCR5 (Zang et al., *J. Neuroimmunol.* 112:174-180 (2001)). There is, therefore, scientific rationale to expect that the blockade of α4-integrins by natalizumab, when added to interferon-β, may have an additive or synergistic effect when added to interferon-β alone.

Natalizumab was also proven efficacious when used to treat patients concurrently receiving treatment with AVONEX®. Prior to receiving natalizumab, these patients were experiencing disease activity despite active treatment. Thus, AVONEX® served as an active control. The study demonstrated that natalizumab, when added to AVONEX®, resulted in a 24% reduction in the risk of disability progression, as measured by changes on the EDSS (p=0.024). The percentage of patients estimated to progress was 23% with natalizumab plus AVONEX® as compared with 29% on AVONEX® alone.

Natalizumab had significant effects on all relapse endpoints examined, when compared to AVONEX® over two years, including a 55% reduction in the annualized relapse rate, with 54% of natalizumab-treated patients relapse-free compared to 32% of patients on AVONEX®. The MRI scans supported these clinically-observed effects. Also, natalizumab, when compared to AVONEX® therapy alone, improved the patients' quality of life, as measured by the physical components of the SF-36, with a trend on the mental component. All these effects were consistent and significant across subgroups defined by baseline demographics and disease activity.

Therapeutic and Risk-Related Properties of Alpha-4 Inhibitory Compounds as a Class Alpha-4 inhibitory compounds other than natalizumab are being developed for use in inflammatory and autoimmune disease indications. At present, at least two small molecule alpha-4 inhibitors are in clinical trials: Roche is conducting phase II trials with R-411 for a multiple sclerosis indication and Glaxo SmithKline is conducting phase IIb trials with GSK693699, also for a multiple sclerosis indication. Both of these molecules are reportedly orally active small molecules.

Further publications acknowledge the properties of alpha-4 inhibitor compounds as a class and suggest that long term blockade of alpha-4-integrins might prevent trafficking of non-pathogenic lymphocytes that are essential for viral immunosurveillance, thus leading to infections or resurgent infections such as PML. Engelhardt et al., European journal of immunology (Germany) August 2005, 35 (8) p2268-73; Van Assch, G. et al.; American journal of physiology. Gastrointestinal and liver physiology (United States) February 2005, 288 (2) pG169-74.

Further, the FDA suspended human trials of both Roche and GSK's alpha-4 inhibitor compounds about one month after the announcement of PML associated with Tysabri use as a precautionary measure. (see Drug Industry Daily, 4(54) "Tysabri Concerns Prompt FDA to Halt Trial of GSK MS drug) The instant invention provides methods of improving the safety of alpha-4 inhibitor compounds in treatment of inflammatory and autoimmune disease as further described herein. Further background in case reports and clinical practice are provided to further illustrate the diagnosis and treatment of PML.

Progressive Multifocal Leukoencephalopathy

PML is an infectious disease of the central nervous system caused by JCV infection of oligodendrocytes. JCV is a human polyoma virus that is believed to infect the majority of healthy individuals at an early age. The seroprevalence of anti-JCV antibodies in healthy individuals has been estimated to range from 20% to 80% depending upon the testing methodology (Knowles et al., *J. Med. Virol.* 71:115-123 (2003)); Knowles and Sasnauskas, *J. Virol. Methods.* 109:47-54 (2003)).

PML occurs predominantly in immunocompromised individuals with an age-adjusted death rate due to PML of 3.3 per million persons (in 1994), 89% of whom were AIDS patients (Holman et al., *Neuroepidemiol.* 17:303-309 (1998)). However, rare PML cases have also been reported in patients with autoimmune disorders who received immunosuppressive therapy; among these, three patients with rheumatoid arthritis (Sponzilli et al., *Neurology* 25:664-668 (1975); Rankin et al., *J. Rheumatol* 22:777-79 (1995); Durez et al., *Arthritis Rheum.* 46 (9S):536 (2002)), one of whom was treated with tumor necrosis factor (TNF) antagonist (Durez et al., *Arthritis Rheum.* 46 (9S):536 (2002)). There was also a report of PML in a Crohn's Disease patient, but the concomitant treatments were not specified (Garrels et al., *Am. J. Neuroradiol.* 17:597-600 (1996)).

The pathology of PML is distinctive and comprises multiple foci of demyelination of varying size from pinpoint lesions to areas of several centimeters. The lesions may occur anywhere but are usually in the cerebral hemispheres, less often in the cerebellum and brain stem and rarely in the spinal cord. The oligodendrocytes in the peripheral zone surrounding an area of demyelination are grossly abnormal. The nuclei of abnormal oligodendrocytes are packed with JC virions. Typically, PML evolves gradually, with impairment of mental function and disturbance of speech and vision. Movement may also be affected. The disease then progresses rapidly and the patient is severely disabled, eventually becoming demented, blind, and paralyzed; coma and death follow.

The presence of JCV in the blood and urine of PML patients and healthy, immunocompetent individuals has been described (Kitamura et al., *J. Infect. Dis.* 161:1128-1133 (1990); Tornatore et al., *Ann. Neurol.* 31:454-462 (1992); Dorries et al., *Virology* 198:59-70 (1994); Sundsfjord et al., *J. Infect. Dis.* 169:485-490 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9(Suppl 1):81-87 (2003)). These findings are neither predictive nor diagnostic of PML in these patients; thus the relationship of blood or urine viral load to PML is unclear.

The clinical presentation of PML is largely dependent upon the size and distribution of the white matter lesions that develop as a result of viral infection, demyelination, and glial cell lysis. However, clinical features of the presentation help differentiate it from the demyelination associated with MS. In contrast to MS, PML involvement of the spinal cord or optic nerves is rare. Instead, about one-third of patients will present with visual field loss or cortical blindness with another third presenting with altered mentation or behavior changes (Dworkin et al., *Curr. Clin. Top. Infect. Dis.* 22:181-195 (2002)). Also unlike MS, hemiparesis is a common presenting symptom. These symptoms are typically subacute in onset and follow a slowly progressive course. Often, patients and their families are the first to notice the onset of PML through changes in the ability to perform routine activities of daily living, even prior to presentation with changes on neurological examination.

MRI is a sensitive tool for the detection of PML lesions in the setting of clinical signs or symptoms, although it may lack specificity. Typical MS lesions, demyelination from other causes (e.g., encephalomyelitis, HIV encephalopathy), gliosis, and edema can often have an appearance similar to early PML lesions. However, as shown in Table 1, there are features of PML lesions that help differentiate them from other etiologies (Post et al., *Am. J. Neuroradiol.* 20:1896-1906 (1999); Yousry et al. *N. Engl. J. Med.* in press (2006); (Berger et al., *Ann. Neurol.* 44:341-349 (1998); Hoffmann et al., *J. Neurol. Neurosurg. Psychiatry* 74:1142-1144 (2003); Langer-Gould et al., *N. Engl. J. Med.* 353:375-381 (2005)).

inversion recovery (FLAIR) MRI reveals hyperintense lesions throughout the supratentorial subcortical white matter (Post et al., *Am. J. Neuroradiol.* 20:1896-1906 (1999)). White matter lesions of PML are typically not surrounded by edema, do not produce a mass effect, and do not enhance in the presence of gadolinium contrast material (Post et al., *Am. J. Neuroradiol.* 20:1896-1906 (1999)). However, hyperintense $T_2$-weighted and FLAIR images are not specific for demyelination and may represent gliosis or edema. Other demyelinating, encephalopathic or ischemic processes such as MS, postviral encephalitis, HIV encephalopathy and infarction, may demonstrate similar non-specific imaging features (Olsen et al., *Radiology* 169:445-448 (1988), Hurley et al., *J. Neuropsychiatry Clin. Neurosci.* 15:1-6 (2003)). The location of lesions and their morphological characteristics, the absence or an atypical presence of gadolinium enhancement on $T_1$-weighted images, and the implementation of magnetization transfer MRI may also help differentiate the demyelination of PML from other demyelinating processes, edema or gliosis (Ernst et al., *Radiology* 210:439-543 (1999); Hurley et al., *J. Neuropsychiatry Clin. Neurosci.* 15:1-6 (2003)).

The clinical diagnosis of PML is confirmed by histological and virological examination of brain material obtained by brain biopsy or at postmortem. Before a biopsy is done, both serum and CSF should be examined for antibodies against

TABLE 1

Differential Diagnosis of MS and PML

| | MS | PML |
| --- | --- | --- |
| Location of new lesions | Mostly focal, may affect entire brain and spinal cord, in white and possibly gray matter; | Diffuse, mainly sub-cortical, rarely periventricular, almost exclusively in white matter, although occasional extension to gray matter seen; |
| | Posterior fossa lesions rarely seen | Posterior fossa frequently involved (cerebellum) |
| Borders | Sharp edges, shapes mostly round or finger-like (especially periventricular), confluent with other single lesions, U-fibers may be involved | Ill-defined edges, infiltrating, irregular in shape, confined to white matter, sparing gray matter, pushing against cortex, U-fibers destroyed |
| Mode of extension | Focal, enlarging of lesions within days/weeks, later decreasing in size within months | Diffuse, asymmetrical, extending homogeneously, no confluence with other lesions, defined to white matter tracks, sparing cortex, continuous progression |
| Mass effect | Acute lesions may show some mass effect | No mass effect even in large lesions (but process is slightly pushing against cortex) |
| T2-weighted sequence | Acute lesions: hyperintense center, isointense ring, discrete hyperintensity outside ring structure; Sub-acute/chronic lesions: hyperintense, no ring structure | Diffuse hyperintense, slightly increased intensity of newly involved areas compared to old areas, little irregular signal intensity of lesions |
| T1-weighted sequence | Acute lesions: densely hypointense (large lesion) or isointense (small lesion), increasing signal intensity over time in 80%, decreasing signal intensity (axonal loss) in about 20% | Slightly hypointense from the onset, signal intensity decreasing over time and along the affected area, no reversion of signal intensity |
| Flair sequence | Hyperintense, sharply delineated | Hyperintensity more obvious, true extension of abnormality more clearly visible than in T2-weighted images |
| Enhancement | Acute lesions: dense homogeneous enhancement, sharp edges Sub-acute lesions: ring-enhancement Chronic lesions: no enhancement | Usually no enhancement even in large lesions, in HIV+ patients some peripheral enhancement possible, especially under therapy |
| Atrophy | Focal atrophy possible due to focal white matter degeneration, no progression | No focal atrophy since extending pathological process is slightly pushing against cortex (extension of tissue) |

MRI analysis can provide a differential diagnosis of MS and PML in patients receiving alpha-4 inhibitor compound therapy. Patients suspected of PML demonstrate the presence of multifocal, asymmetric, white-matter lesions reflective of demyelination by MRI. $T_2$-weighted and fluid-attenuated JCV. A positive result will not confirm PML, but a negative result makes the diagnosis of PML very unlikely. It is rare to detect antibodies against JC in the CSF, and when they are detected, it is suggestive of active multiplication of JCV within the CNS. The brain biopsy or autopsy material can be examined by electron microscopy or immunohistologic electron microscopy. The specimen can also be examined directly for JCV antigen by immunofluorescence or immunoperoxidase staining. Viral isolation of JCV has been reported to be difficult, but may be attempted from primary human fetal glial cells. The presence of the virus in culture is confirmed by electron microscopy, immunofluorescence, or haemagglutination.

PCR analysis of the CSF for JC viral DNA is a highly sensitive and specific test for the diagnosis of PML. The specificity of this test approaches 100%, with a sensitivity ranging from 60% to 90% (Henson et al., *Neurology* 41:1967-1971 (1991); Gibson et al., *J. Med. Virol.* 39:278-281 (1993); Weber et al., *AIDS* 8:49-57 (1994a); Weber et al. *J. Infect. Dis.* 169:1138-1141 (1994b); Vago et al., *J. Acquir. Imm. Defic. Syndr. Hum. Retrovirol.* 12:139-146 (1996)). In cases with a high clinical suspicion of PML and negative CSF results, repeat testing often leads to detection of JC viral DNA. As such, PCR analysis of the CSF for JC viral DNA has grown to be the preferred method to confirm the diagnosis of PML.

Untreated, PML patients have a mortality rate of 30% to 50% during the first three months (Koralnik, *Curr. Opt. Neurol.* 17:365-370 (2004)). Prior to the introduction of highly active antiretroviral treatment (HAART) for HIV, about 10% of patients with PML survived for longer than one year. However, since the advent of HAART, about 50% of patients with PML survive for longer than one year due to restoration of immune function as CD4 counts increased as a result of immune reconstitution inflammatory syndrome (Geschwind et al., *J. Neurovirol.* 7:353-357 (2001); Berger et al., *Ann. Neurol.* 44:341-349 (1998); Clifford et al., *Neurology* 52:623-625 (1999); Tantisiriwat et al., *Clin. Infect. Dis.* 28:1152-1154 (1999)).

Currently, there is no established drug treatment for PML. Various medications have been tested, including acyclovir, idoxuridine, vidarabine, amantadine, adenine arabinoside, cytosine arabinoside (cytarabine), cidofovir, interferon α, interleukin-2 (IL-2), zidovudine, camptothecin, and topotecan (Koralnik, *Curr. Opt. Neurol.* 17:365-370 (2004); Dworkin et al., *Curr. Clin. Top. Infect. Dis.* 22:181-195 (2002); Seth et al., *J. Neurovirol.* 9:236-246 (2003); Collazos, *CNS Drugs* 17:869-887 (2003); Mamidi et al., *J. Neurovirol.* 8:158-167 (2002); Przepiorka et al., *Bone Marrow Transplant;* 20:983-987 (1997); Redington et al., *Arch. Neurol.* 59:712-718 (2002); Padgett et al., *Prog. Clin. Biol. Res.* 105:107-117 (1983)). However, the survival of patients with PML appears to be best correlated with immune reconstitution. In transplant patients with PML, early dosage reduction or/and discontinuation of immunosuppressive therapy was associated with favorable clinical outcome after PML diagnosis (Crowder et al., *Am. J. Transplant* 5:1151-1158 (2005); Shirit et al., *Transpl. Int.* 17:658-665 (2005)).

JC Virus (JCV)

JCV is a member of the class of human polyomavirus, which belong to the Papovaviridae family of small, nonenveloped viruses with a closed, circular double DNA-stranded genome. Polyomaviruses can be distinguished from papillomaviruses by virtue of their smaller virion size and different genomic size and organization. Polyomaviruses are ubiquitous in nature and can be isolated from a number of species. JCV was first isolated from the brain tissue of a patient with progressive multifocal leukoencephalopathy (PML). JCV shares 75% nucleotide sequence homology with the BK human polyomavirus (BKV), which was isolated from the urine of a renal transplant patient with postoperative ureteral stenosis. BKV and JCV each share 70% homology with SV40. The two are not serologically cross-reactive and serologic tests for antibodies are able to distinguish between BKV and JCV (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406).

JCV infection is usually sub-clinical, is almost universal, occurs in childhood, and persists for life. It is estimated that 60-80% of adults in Europe and the United States have antibodies to JCV and that 50% of young adults in the age range of 30-39 years have been infected with JCV. JCV and BKV are believed to circulate independently. It has been proposed that JCV establishes latent infections in the kidney and/or the CNS after a primary infection (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406). During immunosuppression, it has been postulated that latent JCV is reactivated in the kidney, which may lead to viruria. While viruria may have some predictive value for PML, since it does not occur in the majority of PML cases, measuring JCV in the urine alone is not sufficient to diagnose JCV.

When JCV travels through the bloodstream to the brain, it may attack myelin-producing cells. The resulting brain infection produces neurological symptoms which may include ataxia, loss of cognitive function, visual loss, changes in balance and coordination, and loss of sensation. Death commonly occurs within two years following diagnosis.

No specific antiviral therapy that has been proven effective for JCV, and current treatment of immunocompromised patients is primarily supportive and intended to reduce immunosuppression. Cidofovir is currently being studied as a treatment option for transplant patients, and cytarabine can be used in the treatment of PML, although there is currently conflicting data regarding the efficacy of the latter (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406; Salmaggi, *Neurol. Sci.* 22:17-20 (2001)).

The cellular receptor for JCV has been reported to be the serotonin 5HT2(A) receptor (Elphick et al., *Science* 306:1380-1383 (2004)). In vitro, the antipsychotic medications chlorpromazine and clozapine were shown to block the serotonin 5HT2(A) receptor and to block JCV cell entry. Unfortunately, however, chlorpromazine and clozapine have such significant side effects and toxicities, e.g., extrapyramidal symptoms and the possibility of bone marrow dyscrasias that they may be problematic to use clinically. The invention provides that newer atypical antipsychotics, such as zisprasidone, risperidone, and olanzapine—medicines with much better side effect and toxicity profiles than the older antipsychotics—are significantly more potent 5HT2(A) receptor antagonists in vitro than chlorpromazine and clozapine.

A wide variety of serological tests are available to detect JCV, e.g., complement-fixation (CFT), haemagglutination-inhibition (HAI), enzyme-linked immunoassay (EIA), radioimmunoassay (RIA), particle agglutination, immunofluorescence (IF), single radial hemolysis, and Western blot. The sensitivity and specificity varies greatly between different techniques. Most techniques will detect all classes of antibody, whereas some assays e.g., RIA, EIA, and IF can be designed to detect one specific class, for example, IgM, IgG, or IgA.

Patient Selection Based on Safety and Efficacy

Appropriate patient selection will help maximize the benefit-risk profile of alpha-4 inhibitor compounds. Natalizumab, as an indicator, has demonstrated efficacy in treatment-naïve patients with mild to moderate disability (EDSS 0 to 5.0) with recent clinical disease activity (for example, one relapse in the year prior to study entry). It has also demonstrated efficacy in patients with mild to moderate disability with continuing disease activity despite treatment with β-interferon (for example, one relapse in the year prior to study entry, while receiving AVONEX®).

The benefit/risk ratio is altered in certain other patient populations. Patients without evidence of relapsing disease, that is, without evidence of inflammatory activity clinically or by MRI, such as those with relatively "benign" inactive disease, or chronic-progressive forms of MS, were excluded from the Phase 3 trials, thus, natalizumab has not been completely evaluated in these cohorts. The benefit-risk is also further altered in patients with a single clinical event without features suggestive of MS.

Patients who are clinically stable on current therapy also have an altered benefit/risk ratio. If safety or tolerability concerns exist on the current treatment, or imaging studies indicate active inflammatory sub-clinical disease, natalizumab treatment would be appropriate. In considering the benefit-risk ratio, it should be considered whether the patient has previously suffered a hypersensitivity reaction or developed persistent antibodies to natalizumab. Re-dosing of natalizumab following a hypersensitivity reaction was not assessed in Phase 3 trials. Persistent antibodies against natalizumab lead to a loss of efficacy and an increase in infusion-related side effects. Patients who are immunocompromised from any cause, including use of immunosuppressant medications have an independent risk factor for PML and other opportunistic infections and should not receive alpha-4 inhibitor therapy.

Another criteria for patient selection is a pre-infusion checklist used by the infusion nurse to facilitate early detection of PML and minimize inappropriate use of natalizumab. The checklist prompts the nurse to ask the patient about continuously worsening neurological symptoms that have persisted over several days, e.g., new or sudden decline in thinking, eyesight, balance, or strength. If a patient reports having any symptoms described by the checklist, the nurse is instructed not to administer natalizumab and to refer the patient to his or her physician.

This checklist also ascertains that the patient will be receiving alpha-4 inhibitor therapy for the treatment of relapsing MS, has never been diagnosed with PML, and is not currently experiencing any continuously worsening symptoms that have persisted over several days. It further ascertains that the patient is not known to be suffering from HIV or a hematologic malignancy, nor has had an organ transplant. It confirms that the patient is not currently receiving treatment with an anti-neoplastic, immunomodulatory, or immunosuppressive agent and that the patient has read the patient information leaflet provided with the alpha-4 inhibitor compound, which is further described in Example 2.

Informing Patients and Caregivers

In the US, patients with MS receive medical treatment by a relatively small group of physicians, primarily neurologists. Approximately 6,000 physicians treat 90% of patients with MS. This is in contrast to 170,000 family practitioners that treat primary care diseases in the US. A dedicated force of physicians and sales representatives can interact with neurologists and other healthcare professionals who care for patients with MS. Consequently, nearly all physicians who will prescribe alpha-4 inhibitor therapy for MS can readily be contacted.

Because PML is a disease of the central nervous system, the targeted prescribers of alpha-4 inhibitor therapies are also the best-qualified physicians to diagnose and manage PML. Neurologists have the expertise to monitor subjects for signs and symptoms indicative of PML and select appropriate diagnostic tests to diagnose a patient with PML.

Also, patients with MS are knowledgeable about their treatment options. They are generally a young and highly-motivated. In a recent survey, 94% to 99% of patients with MS were aware of their treatment options, including β-interferons and glatiramer acetate (Biogen Idec). During the period when natalizumab was available commercially, 79% of patients with MS were aware of the introduction of natalizumab treatment. Also, feedback from patients with MS indicated that the risk of PML with natalizumab has been broadly disseminated in the MS community. Thus, the targeted patient population is likely to want to learn more about the risks of PML with alpha-4 inhibitor therapies.

Accordingly, the present invention provides for informing the prescribing physician and the patient about the mental and physical symptoms of progressive multifocal leukoencephalopathy and instructing the patient to report to the physician in the presence of at least one symptom. These informational efforts will provide relapsing MS patients and their physicians with the information they need to make informed benefit-risk decisions about the use of this highly effective therapy, while actively managing recognized risks. The present invention also provides informational tools for patients and physicians to promote informed benefit-risk decisions, to ensure appropriate use of alpha-4 inhibitor compounds, and to reinforce the importance of early detection of PML through clinical vigilance. For example, the present invention provides protocols for informing physicians and patients of the risks of alpha-4 inhibitor compounds treatment and for actively assessing and managing these risks on an ongoing basis. These protocols are based upon current medical and scientific knowledge of PML and information gained from the safety evaluation of natalizumab-treated patients.

This information provides a setting wherein appropriate patients receive natalizumab. Accordingly, the present invention provides that patients and physicians receive significant information regarding the risks associated with alpha-4 inhibitor compounds so that informed benefit-risk decisions can be made regarding initiation of alpha-4 inhibitor compound treatment.

The invention also provides that the prescription for an alpha-4 inhibitor compound serves as an enrollment form for physicians and for patients that collects information regarding risk factors for PML, and requires an acknowledgement by physicians and patients that they understand the risks associated with alpha-4 inhibitor compound treatment.

A surveillance program monitors patients receiving natalizumab treatment by routinely assessing them for PML, using the opportunity afforded through the periodic interactions between the heath care providers and patients at the time of infusion. In an embodiment, these periodic interactions occur approximately once a month. Patients with possible PML are thus rapidly identified, so that alpha-4 inhibitor therapy can be immediately discontinued and the proper assessments completed. This information, surveillance, and monitoring program provide timely information regarding safety issues related to alpha-4 inhibitor therapy.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. The specification is most thoroughly understood in light of the references cited herein.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth. It is further to be understood that reference to an alpha-4 inhibitor compound includes a plurality of such compounds unless the context clearly dictates otherwise. An alpha-4 inhibitor compound may be a small molecule, derivative or equivalent thereof.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Efficacy of Natalizumab

The efficacy of natalizumab over a two year period has been demonstrated in two Phase 3 trials (Polman et al., N. Engl. J. Med. in press (2006); Rudick et al. N. Engl. J. Med.in press (2006)). In one study, natalizumab was given as monotherapy to treatment-naïve MS patients and its efficacy was compared to placebo. In the other study, natalizumab was given to patients who were experiencing relapses despite concurrent AVONEX® therapy and its efficacy was compared to that of AVONEX (interferon β-1a) plus placebo. Data through two years have confirmed the benefit that led to accelerated approval at one year. These data show that natalizumab is highly efficacious in delaying the time to onset of sustained progression of disability, in reducing annualized relapse rate, in attenuating MRI lesions, and in improving the quality of life of patients compared both to placebo and the active AVONEX® control group.

Both Phase 3 studies had similar designs. In the monotherapy study, 942 untreated relapsing remitting MS patients were randomized to receive natalizumab or placebo for 120 weeks (30 infusions) using a 2:1 allocation. In the add-on study, 1,171 patients who had been receiving weekly intramuscular injections of 30 μg AVONEX®, but who had relapsed despite this treatment, were randomized using a 1:1 allocation to add natalizumab or placebo to their regimen, also for 120 weeks.

Efficacy parameters included EDSS scores, MS relapses, brain MRI scans, MSFC scores, visual function tests, and quality of life. EDSS and MSFC were measured every 12 weeks, brain MRI scans and quality of life questionnaires at baseline and every year, and MS relapses on an ongoing basis.

Treatment with natalizumab as monotherapy in treatment-naïve patients had profound effects on the time to onset of sustained progression in disability and on annualized relapse rate, the two primary endpoints, as shown in Table 2. These significant effects were confirmed versus AVONEX® alone.

TABLE 2

Efficacy of Natalizumab in Phase 3 Studies

| | Monotherapy | | Add-on therapy | |
|---|---|---|---|---|
| | Placebo | 300 mg natalizumab | AVONEX + placebo | AVONEX + 300 mg natalizumab |
| Number of patients | 315 | 627 | 582 | 589 |
| Percentage of patients with sustained progression of disability | 29% | 17% | 29% | 23% |
| Hazard ratio (95% confidence interval) | 0.58 (0.43, 0.77) | | 0.76 (0.61, 0.96) | |
| Risk reduction | 42% | | 24% | |
| p-value | $p < 0.001$ | | $p = 0.024$ | |
| Annualized relapse rate | 0.733 | 0.235 | 0.749 | 0.336 |
| Relative reduction | 68% | | 55% | |
| p-value | $p < 0.001$ | | $p < 0.001$ | |

The patient population in the two Phase 3 studies were relapsing MS patients according to the criteria of the International Panel on the Diagnosis of Multiple Sclerosis (McDonald et al., *Ann. Neurol.* 50:121-127 (2001)). It encompassed a broad range of ages and disease severity, and represented the current relapsing MS population with active disease, consistent with the approved indication. Patients with primary- or secondary-progressive MS were excluded.

The patient populations targeted for the two studies differed. Patients in the monotherapy study were essentially naïve to treatment with an immunomodulatory drug for MS. Specifically, patients may not have had treatment with any immunomodulator (β-interferon or glatiramer acetate) for a period longer than six months and not within six months of the beginning of the study. The result was a young, mostly female, MS population with a moderate degree of baseline disease activity (typical of the general MS population), very few of whom had tried another immunomodulator prior to study entry.

Patients in the add-on therapy study were required to have received AVONEX® for the previous year and to have had a relapse during that time while on AVONEX® treatment. This resulted in a population somewhat older than that in the monotherapy study, with a longer disease duration. However, patients in the add-on therapy study had a similar degree of disease activity as those in the monotherapy study, despite AVONEX® treatment.

Example 2

Caregiver and Patient Information

With the introduction of a small molecule alpha-4 inhibitor as a new therapeutic agent, the enrollment and safety procedures described herein will very likely be implemented in the same or similar fashion as that for natalizumab. Prior to starting alpha-4 inhibitoyr compound treatment, the physician will provide the patient with the Patient Information Leaflet, will ask the patient to read it, and will discuss the information with the patient. The Patient Information Leaflet is intended to provide information to patients with MS on the risks of alpha-4 inhibitory compound treatment, including the risk of PML. In addition, the leaflet instructs patients to promptly report any continuously worsening, i.e., progressing, neurological symptoms to their physician, thereby reinforcing the importance of early detection of PML. The Patient Information Leaflet will be widely disseminated. In addition, to distribution to prescribers and infusion centers, the leaflet will be available on the internet and distributed to patient groups such as the National Multiple Sclerosis Society (NMSS).

Once the decision to use an alpha-4 inhibitory compound is made, the physician and patient will complete the enrollment form. The enrollment form includes an alpha-4 inhibitory compound prescription and a Patient-Physician Acknowledgement. The physician and patient will sign the Patient-Physician Acknowledgment to document that they discussed and understood alpha-4 inhibitory compound benefits and risks, including the risk of PML, and that the physician is prescribing alpha-4 inhibitory compound for the treatment of relapsing MS.

By signing the Patient-Physician Acknowledgement, the physician also acknowledges that he or she has read the full prescribing information for alpha-4 inhibitory compound, is aware that an alpha-4 inhibitory compound is associated with an increased risk of PML, which causes death or disability, has discussed the risks and benefits of alpha-4 inhibitory compound treatment with his or her patient, and is prescribing the alpha-4 inhibitory compound for the treatment of relapsing MS. The physician also acknowledges that the patient is not immunocompromised, and has instructed the patient to promptly report to his or her physician any continuously worsening, i.e., progressing, symptoms that persist over several days.

By signing the Patient-Physician Acknowledgement, the patient acknowledges that he or she has read the Patient Information Leaflet, is aware that the alpha-4 inhibitory compound is associated with an increased risk of PML, which causes death and disability, has discussed the risks and benefits of the alpha-4 inhibitory compound with his or her physician, and understands that it is important to promptly report to his or her physician any continuously worsening, i.e., progressing, symptoms lasting over several days. The patient and physician information are entered into a central database, thus initiating enrollment into the alpha-4 inhibitory compound risk management program.

Each enrolled patient is assigned a case manager who can answer questions about the alpha-4 inhibitory compound, provide insurance coverage research, and match the patient to an appropriate infusion center. These services will be provided again upon alpha-4 inhibitory compound re-introduction and are another reason for patients and physicians to use the enrollment form. In addition, informational materials for an alpha-4 inhibitory compound will inform physicians of the need to use the enrollment form for all alpha-4 inhibitory compound-treated patients and sales representatives who interface directly with prescribing physicians will be trained to reinforce the importance of using the form with all neurologists.

What is claimed is:

1. A method of using an alpha-4 inhibitor compound to treat a patient with an inflammatory, or autoimmune disease comprising:
   (a) administering a pharmaceutically effective amount of the alpha-4 inhibitor compound;
   (b) monitoring the patient for at least one indicator of progressive multifocal leukoencephalopathy; and
   (c) discontinuing administration of the alpha-4 inhibitor compound when at least one indicator of progressive multifocal leukoencephalopathy is present;
   wherein the monitoring improves safety of treatment;
   wherein the alpha-4 inhibitor compound is a compound of Formula V, a pharmaceutically acceptable salt or ester of any of the foregoing:

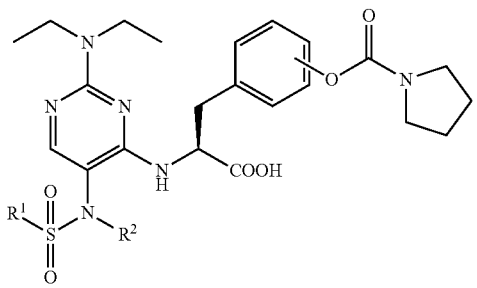

wherein:
   $R^1$ is selected from the group consisting of $C_1$ to $C_4$ alkyl and $C_1$ to $C_4$ haloalkyl; and
   $R^2$ is selected from the group consisting of $C_1$ to $C_4$ alkyl, $C_2$ to $C_4$ alkenyl, $C_2$ to $C_4$ alkynyl, $C_3$-$C_6$ cycloalkyl and benzyl.

2. The method of claim 1, wherein the disease comprises multiple sclerosis.

3. The method of claim 2, wherein the multiple sclerosis is selected from relapsing remitting, secondary progressive, primary progressive, and chronic progressive multiple sclerosis.

4. The method of claim 1, wherein the disease is chosen from inflammatory bowel disease and rheumatoid arthritis.

5. The method of claim 4, wherein the inflammatory bowel disease comprises Crohn's Disease.

6. The method of claim 1, wherein the monitoring detects JC virus in the patient's urine, blood, and/or cerebrospinal fluid.

7. The method of claim 6, wherein the monitoring comprises serially removing samples of the patient's blood, measuring an amount of IgG antibodies to JC virus in the samples, and comparing the amount of the antibodies in the samples to each other.

8. The method of claim 7, wherein the monitoring further comprises measuring an amount of IgM antibodies to JC virus in the samples, and comparing the amount of the IgM and IgG antibodies in the samples to each other.

9. The method of claim 7, wherein the monitoring detects seroconversion and/or an increasing titer of JC virus in the patient's blood, and further comprises
(a) removing a sample of the patient's cerebrospinal fluid when comparison of the blood samples detects seroconversion and/or an increasing titer of JC virus; and
(b) testing the cerebrospinal fluid for JC virus.

10. The method of claim 1, wherein the monitoring comprises testing for at least one symptom chosen from clinical and radiologic symptoms of progressive multifocal leukoencephalopathy.

11. The method of claim 10, wherein the testing for clinical symptoms comprises testing for new or progressing neurological symptoms.

12. The method of claim 11, wherein the neurological symptoms comprise one or more of central blindness, mental confusion, personality change, and dyskinesia.

13. The method of claim 10, wherein the testing for radiologic symptoms comprises performing a Gd-enhanced magnetic resonance imaging scan.

14. The method of claim 1, further comprising, when at least one indicator of progressive multifocal leukoencephalopathy is present, providing antiviral therapy.

15. The method of claim 14, wherein the antiviral therapy comprises administering at least one therapeutically effective dose of an antiviral agent selected from cytosine arabinoside (cytarabine), cidofovir, and a serotonin antagonist.

16. The method of claim 15, wherein the serotonin antagonist comprises a 5HT2a antagonist.

17. The method of claim 1, wherein the alpha-4 inhibitor compound is monotherapy without an immunosuppressive or antineoplastic agent.

18. The method of claim 17, wherein the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluorodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

19. The method of claim 18, wherein the immunosuppressive agent comprises a β-interferon.

20. A method of using an alpha-4 inhibitor compound to treat a patient with an inflammatory or autoimmune disease comprising:
(a) removing a sample of blood from the patient;
(b) testing serum or plasma of the sample for IgG antibodies to JC virus;
(c) initiating treatment of the patient with the alpha-4 inhibitor compound, if the sample is negative for IgG antibodies to JC virus;
(d) monitoring the patient for at least one indicator of progressive multifocal leukoencephalopathy; and
(e) discontinuing administration of the alpha-4 inhibitor compound when at least one indicator of progressive multifocal leukoencephalopathy is present;
wherein the testing and monitoring improve safety of the treatment;
wherein the alpha-4 inhibitor compound is a compound of Formula V, a pharmaceutically acceptable salt or ester of any of the foregoing:

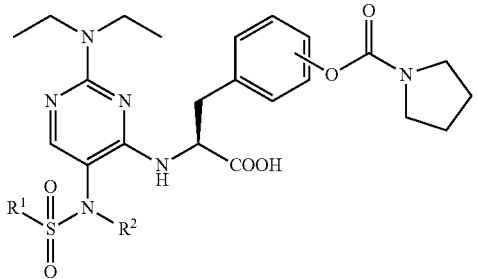

wherein:
$R^1$ is selected from the group consisting of $C_1$ to $C_4$ alkyl and $C_1$ to $C_4$ haloalkyl; and
$R^2$ is selected from the group consisting of $C_1$ to $C_4$ alkyl, $C_2$ to $C_4$ alkenyl, $C_2$ to $C_4$ alkynyl, $C_3$-$C_6$ cycloalkyl and benzyl.

21. The method of claim 20, wherein the disease comprises multiple sclerosis.

22. The method of claim 21, wherein the multiple sclerosis is selected from relapsing remitting, secondary progressive, primary progressive, and chronic progressive multiple sclerosis.

23. The method of claim 20, wherein the disease is chosen from inflammatory bowel disease or rheumatoid arthritis.

24. The method of claim 23, wherein the inflammatory bowel disease comprises Crohn's Disease.

25. The method of claim 20, wherein the disease comprises asthma.

26. The method of claim 20, further comprising testing the serum or plasma of the sample for IgM antibodies to JC virus and initiating treatment if the serum or plasma is negative for both. IgG and IgM antibodies to JC virus.

27. The method of claim 20 wherein the monitoring detects JC virus in the patient's urine, blood, and/or cerebrospinal fluid.

28. The method of claim 27, wherein the monitoring comprises serially removing samples of the patient's blood, measuring an amount of IgG antibodies to JC virus in the samples, and comparing the amount of the antibodies in the samples to each other.

29. The method of claim 28, wherein the monitoring further comprises measuring an amount of IgM antibodies to JC virus in the samples, and comparing the amount of the IgM and IgG antibodies in the samples to each other.

30. The method of claim 28, wherein the monitoring detects seroconversion and/or an increasing titer of JC virus in the patients blood, and further comprises
   (a) removing a sample of the patient's cerebrospinal fluid when comparison of the blood samples detects seroconversion and/or an increasing titer of JC virus; and
   (b) testing the cerebrospinal fluid for JC virus.

31. The method of claim 20, wherein the monitoring comprises testing for at least one symptom chosen from clinical and radiologic symptoms of progressive multifocal leukoencephalopathy.

32. The method of claim 31, wherein the testing for clinical symptoms comprises testing for new or progressing neurological symptoms.

33. The method of claim 32, wherein the neurological symptoms comprise one or more of central blindness, mental confusion, personality change, and dyskinesia.

34. The method of claim 31, wherein the testing for radiologic symptoms comprises performing a Gd-enhanced magnetic resonance imaging scan.

35. The method of claim 20, further comprising, when at least one indicator of progressive multifocal leukoencephalopathy is present, providing antiviral therapy.

36. The method of claim 35, wherein the antiviral therapy comprises administering at least one therapeutically effective dose of an antiviral agent selected from cytosine arabinoside (cytarabine), cidofovir, and a serotonin antagonist.

37. The method of claim 36, wherein the serotonin antagonist comprises a 5HT2a antagonist.

38. The method of claim 20, wherein the alpha-4 inhibitor compound is a monotherapy without an immunosuppressive or antineoplastic agent.

39. The method of claim 38, wherein the immunosuppressive or antineoplastic agent is selected from one or more of chlorambucil, melphalan, 6-mercaptopurine, thiotepa, ifosfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, flurorodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

40. The method of claim 39, wherein the immunosuppressive agent comprises a β-interferon.

41. A method of using an alpha-4 inhibitor compound to a patient with an inflammatory or autoimmune disease comprising:
   (a) removing a sample of blood from the patient;
   (b) testing serum or plasma of the sample for IgG antibodies to JC virus;
   (c) initiating treatment of the patient with the alpha-4 inhibitor compound, if the sample is positive for IgG antibodies to JC virus;
   (d) monitoring the patient for at least one indicator of progressive multifocal leukoencephalopathy; and
   (e) discontinuing administration of the alpha-4 inhibitor compound when at least one indicator of progressive multifocal leukoencephalopathy is present;
wherein the testing and monitoring improves the safety of the treatment;
   wherein the alpha-4 inhibitor compound is a compound of Formula V, a pharmaceutically acceptable salt or ester of any of the foregoing:

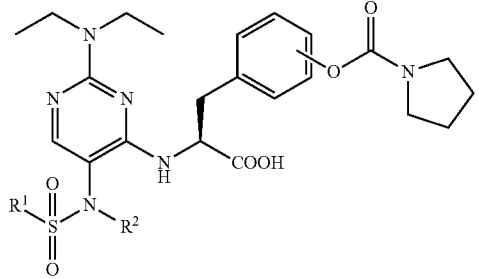

wherein:
   $R^1$ is selected from the group consisting of $C_1$ to $C_4$ alkyl and $C_1$ to $C_4$ haloalkyl; and
   $R^2$ is selected from the group consisting of $C_1$ to $C_4$ alkyl, $C_2$ to $C_4$ alkenyl, $C_2$ to $C_4$ alkynyl, $C_3$-$C_6$ cycloalkyl and benzyl.

42. The method of claim 41, wherein the disease comprises multiple sclerosis.

43. The method of claim 42, wherein the multiple sclerosis is selected from relapsing remitting, secondary progressive, primary progressive, and chronic progressive multiple sclerosis.

44. The method of claim 41, wherein the disease is chosen from inflammatory bowel disease and rheumatoid arthritis.

45. The method of claim 44, wherein the inflammatory bowel disease comprises Crohn's Disease.

46. The method of claim 41, wherein the disease comprises asthma.

47. The method of claim 41, wherein the monitoring detects JC virus in the patient's urine, blood, and/or cerebrospinal fluid.

48. The method of claim 47, wherein the monitoring comprises serially removing samples of the patient's blood, measuring an amount of IgG antibodies to JC virus in the samples, and comparing the amount of the antibodies in the samples to each other.

49. The method of claim 48, wherein the monitoring further comprises measuring an amount of IgM antibodies to JC virus in the samples, and comparing the amount of the IgM and IgG antibodies in the samples to each other.

50. The method of claim 48, wherein the monitoring detects seroconversion and/or an increasing titer of JC virus in the patient's blood, and further comprises
   (a) removing a sample of the patient's cerebrospinal fluid when comparison of the blood samples detect seroconversion and/or an increasing titer of JC virus; and
   (b) testing the cerebrospinal fluid for of JC virus.

51. The method of claim 41, wherein the monitoring comprises testing for at least one symptom chosen from clinical and radiologic symptoms of progressive multifocal leukoencephalopathy.

52. The method of claim 51, wherein the testing for clinical symptoms comprises testing for new or progressing neurological symptoms.

53. The method of claim 52, wherein the neurological symptoms comprise one or more of central blindness, mental confusion, personality change, and dyskinesia.

54. The method of claim 51, wherein the testing for radiologic symptoms comprises performing a Gd-enhanced magnetic resonance imaging scan.

55. The method of claim 41, further comprising, when at least one indicator of progressive multifocal leukoencephalopathy is present, providing antiviral therapy.

56. The method of claim 55, wherein the antiviral therapy comprises administering at least one therapeutically effective dose of an antiviral agent selected from cytosine arabinoside (cytarabine), cidofovir, and a serotonin antagonist.

57. The method of claim 56, wherein the serotonin antagonist comprises a 5HT2a antagonist.

58. The method of claim 41, wherein the alpha-4 inhibitor compound is a monotherapy without an immunosuppressive or antineoplastic agent.

59. The method of claim 58, wherein the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-I, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

60. The method of claim 59, wherein the immunosuppressive agent comprises a β-interferon.

61. A method of using an alpha-4 inhibitor compound to treat a patient with an inflammatory, or autoimmune disease comprising:
   (a) removing a sample of blood from the patient;
   (b) testing the sample for IgG antibodies to JC virus;
   (c) initiating treatment of the patient with the alpha-4 inhibitor compound, if the sample is positive for IgG antibodies to JC virus;
   (d) educating a prescribing physician about mental and physical symptoms of progressive multifocal leukoencephalopathy;
   (e) educating the patient about the mental and physical symptoms of progressive multifocal leukoencephalopathy and instructing the patient to report to the physician when at least one symptom is present;
   (f) monitoring the patient for at least one indicator of progressive multifocal leukoencephalopathy; and
   (g) discontinuing administration of alpha-4 inhibitor compound when at least one indicator of progressive multifocal leukoencephalopathy is present;
wherein the testing, education, and monitoring improve safety of treatment;
wherein the alpha-4 inhibitor compound is a compound of Formula V, a pharmaceutically acceptable salt or ester of any of the foregoing:

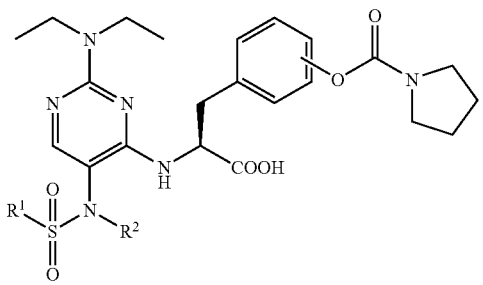

V wherein:
   $R^1$ is selected from the group consisting of $C_1$ to $C_4$ alkyl and $C_1$ to $C_4$ haloalkyl; and
   $R^2$ is selected from the group consisting of $C_1$ to $C_4$ alkyl, $C_2$ to $C_4$ alkenyl, $C_2$ to $C_4$ alkynyl, $C_3$-$C_6$ cycloalkyl and benzyl.

62. The method of claim 61, wherein the disease comprises multiple sclerosis.

63. The method of claim 62, wherein the multiple sclerosis is selected from relapsing remitting, secondary progressive, primary progressive, and chronic progressive multiple sclerosis.

64. The method of claim 61, wherein the disease is chosen from inflammatory bowel disease and rheumatoid arthritis.

65. The method of claim 64, wherein the inflammatory bowel disease comprises Crohn's Disease.

66. The method of claim 61, wherein the disease comprises asthma.

67. The method of claim 61, wherein the monitoring detects JC virus in the patient's urine, blood, and/or cerebrospinal fluid.

68. The method of claim 67, wherein the monitoring comprises serially removing samples of the patient's blood, measuring an amount of IgG antibodies to JC virus in the samples, and comparing the amount of the antibodies in the samples to each other.

69. The method of claim 68, wherein the monitoring further comprises measuring an amount of IgM antibodies to JC virus in the samples, and comparing the amount of the IgM and IgG antibodies in the samples to each other.

70. The method of claim 68, wherein the monitoring detects seroconversion and/or an increasing titer of JC virus in the patient's blood, and further comprises
(a) removing a sample of the patient's cerebrospinal fluid when comparison of the blood samples detect seroconversion and/or an increasing titer of JC virus; and
(b) testing the cerebrospinal fluid for JC virus.

71. The method of claim 61, wherein the monitoring comprises testing for at least one symptom chosen from clinical and radiologic symptoms of progressive multifocal leukoencephalopathy.

72. The method of claim 71, wherein the testing for clinical symptoms comprises testing for new or progressing neurological symptoms.

73. The method of claim 72, wherein the neurological symptoms comprise one or more of central blindness, mental confusion, personality change, and dyskinesia.

74. The method of claim 71, wherein the testing for radiologic symptoms comprises performing a Gd-enhanced magnetic resonance imaging scan.

75. The method of claim 61, further comprising, when at least one indicator of progressive multifocal leukoencephalopathy is present, providing antiviral therapy.

76. The method of claim 75, wherein the antiviral therapy comprises administering at least one therapeutically effective dose of an antiviral agent selected from cytosine arabinoside (cytarabine), cidofovir, and a serotonin antagonist.

77. The method of claim 76, wherein the serotonin antagonist comprises a 5HT2a antagonist.

78. The method of claim 61, wherein the alpha-4 inhibitor compound is a monotherapy without an immunosuppressive or antineoplastic agent.

79. The method of claim 78 wherein the immunosuppressive or antineoplastic agent is selected from one or more of chlorambucil, melphalan, 6-mercaptopurine, thiotepa, ifosfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

80. The method of claim 79, wherein the immunosuppressive agent comprises a β-interferon.

\* \* \* \* \*